United States Patent
Nitta et al.

(10) Patent No.: US 9,797,972 B2
(45) Date of Patent: Oct. 24, 2017

(54) IMAGE PROCESSING APPARATUS, MAGNETIC RESONANCE IMAGING APPARATUS, AND IMAGE PROCESSING METHOD

(71) Applicant: TOSHIBA MEDICAL SYSTEMS CORPORATION, Otawara-shi, Tochigi (JP)

(72) Inventors: Shuhei Nitta, Tokyo (JP); Tomoyuki Takeguchi, Kanagawa (JP); Nobuyuki Matsumoto, Tokyo (JP); Masahiro Sekine, Tokyo (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 157 days.

(21) Appl. No.: 14/720,257

(22) Filed: May 22, 2015

(65) Prior Publication Data

US 2015/0253407 A1    Sep. 10, 2015

Related U.S. Application Data

(63) Continuation of application No. PCT/JP2013/081565, filed on Nov. 22, 2013.

(30) Foreign Application Priority Data

Nov. 22, 2012  (JP) ................................ 2012-256650

(51) Int. Cl.
*G06K 9/62* (2006.01)
*G01R 33/561* (2006.01)
(Continued)

(52) U.S. Cl.
CPC .......... *G01R 33/5615* (2013.01); *A61B 5/055* (2013.01); *A61B 5/7425* (2013.01);
(Continued)

(58) Field of Classification Search
CPC combination set(s) only.
See application file for complete search history.

(56) References Cited

U.S. PATENT DOCUMENTS 6,381,296 B1   4/2002  Nishiura
7,280,862 B2  10/2007  Gupta et al.
(Continued)

FOREIGN PATENT DOCUMENTS

JP  2002-140689   5/2002
JP  2006-55641    3/2006
(Continued)

OTHER PUBLICATIONS

International Search Report for PCT/JP2013/081565, dated Dec. 24, 2013, 2 pages.
(Continued)

*Primary Examiner* — Anand Bhatnagar
(74) *Attorney, Agent, or Firm* — Nixon & Vanderhye P.C.

(57) ABSTRACT

An image processing apparatus according to an embodiment includes processing circuitry. The processing circuitry is configured to generate, from three-dimensional medical image data, a first cross-sectional image and a second cross-sectional image intersecting the first cross-sectional image and is configured to change display locations of the first cross-sectional image and the second cross-sectional image on a display, in conjunction with a change in an intersecting location of the first and the second cross-sectional images.

14 Claims, 12 Drawing Sheets

(51) Int. Cl.
*A61B 5/055* (2006.01)
*A61B 5/00* (2006.01)
*A61B 6/00* (2006.01)
*G01R 33/48* (2006.01)
*G01R 33/54* (2006.01)
*G01R 33/56* (2006.01)
*G06T 7/00* (2017.01)
*G06T 19/00* (2011.01)
*A61B 6/03* (2006.01)
*A61B 8/08* (2006.01)

(52) U.S. Cl.
CPC .......... *A61B 6/466* (2013.01); *A61B 6/5223* (2013.01); *G01R 33/4822* (2013.01); *G01R 33/543* (2013.01); *G01R 33/5608* (2013.01); *G06K 9/6232* (2013.01); *G06T 7/0012* (2013.01); *G06T 19/00* (2013.01); *A61B 5/0037* (2013.01); *A61B 6/03* (2013.01); *A61B 6/503* (2013.01); *A61B 8/0883* (2013.01); *A61B 8/483* (2013.01); *A61B 8/523* (2013.01); *G06T 2200/24* (2013.01); *G06T 2207/10088* (2013.01); *G06T 2207/30048* (2013.01); *G06T 2210/41* (2013.01); *G06T 2219/008* (2013.01); *G06T 2219/028* (2013.01)

(56) References Cited

U.S. PATENT DOCUMENTS

| | | | | |
|---|---|---|---|---|
| 7,684,604 | B2 | 3/2010 | Bystrov et al. | |
| 7,723,987 | B2* | 5/2010 | Bito | G01R 33/4833 324/307 |
| 8,340,374 | B2* | 12/2012 | Yamagata | A61B 6/032 382/100 |
| 8,675,945 | B2* | 3/2014 | Barnhorst | G06F 19/321 382/131 |
| 9,179,893 | B2* | 11/2015 | Endo | A61B 8/4416 |
| 9,414,807 | B2* | 8/2016 | Hamada | A61B 8/14 |
| 9,501,829 | B2* | 11/2016 | Wu | G06F 19/321 |
| 2010/0007663 | A1 | 1/2010 | Matsumoto | |
| 2011/0282207 | A1* | 11/2011 | Hashimoto | A61B 8/0883 600/443 |
| 2011/0313291 | A1* | 12/2011 | Chono | A61B 8/08 600/440 |
| 2012/0089016 | A1* | 4/2012 | Mizuno | G06T 11/206 600/425 |

FOREIGN PATENT DOCUMENTS

| | | |
|---|---|---|
| JP | 4018303 | 9/2007 |
| JP | 2007-534411 | 11/2007 |
| JP | 2010-17314 | 1/2010 |
| JP | 2010-273792 | 12/2010 |
| JP | 2011-239890 | 12/2011 |

OTHER PUBLICATIONS

Written Opinion of the IDS (non-English) for PCT/JP2013/081565, dated Dec. 24, 2013, 3 pages.
Kramer, "CMR Image Acquisition Protocols", Society for Cardiovascular Magnetic Resonance (SCMR),, version 1.0, Mar. 2007, 31 pages.
Office Action dated Feb. 27, 2017 in CN 201380060907.0.

* cited by examiner

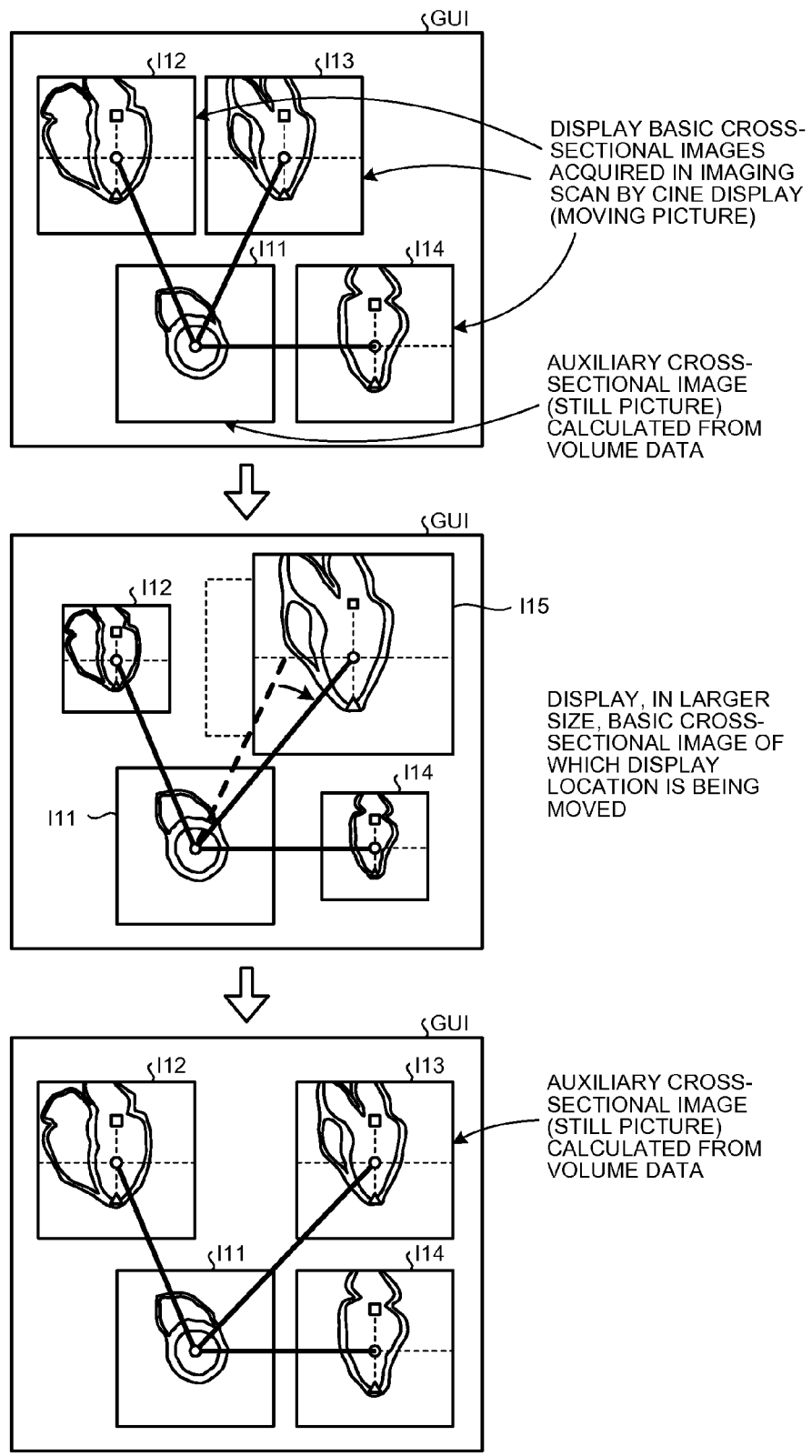

IMAGE PROCESSING APPARATUS, MAGNETIC RESONANCE IMAGING APPARATUS, AND IMAGE PROCESSING METHOD

CROSS-REFERENCE TO RELATED APPLICATIONS

This application is a continuation of PCT international application Ser. No. PCT/JP2013/081565 filed on Nov. 22, 2013 which designates the United States, incorporated herein by reference, and which claims the benefit of priority from Japanese Patent Applications No. 2012-256650, filed on Nov. 22, 2012, incorporated herein by reference.

FIELD

Embodiments described herein relate generally to an image processing apparatus, a magnetic resonance imaging apparatus, and an image processing method.

BACKGROUND

Conventionally, when an image taking process is performed by a medical image diagnosis apparatus such as a magnetic resonance imaging apparatus, an X-ray Computed Tomography (CT) apparatus, or an ultrasound diagnosis apparatus, three-dimensional data is acquired by performing an image taking process on a target site so that cross-sectional images are generated from the acquired data, in some situations.

For example, when the image taking process is performed on the heart, a "basic cross-sectional image" such as a vertical long-axis image, a horizontal long-axis image, a two-chamber cross-sectional image, a three-chamber cross-sectional image, or a four-chamber cross-sectional image is used for diagnosis. In order to appropriately set an image taking location of such a basic cross-sectional image, for example, the medical image diagnosis apparatus acquires the three-dimensional data prior to an imaging scan performed to acquire images for diagnosis purposes, and further generates the "basic cross-sectional image" and an "auxiliary cross-sectional image" used for setting the "basic cross-sectional image" from the acquired three-dimensional data. After that, the medical image diagnosis apparatus causes a display to display the generated cross-sectional images and sets the image taking location of the "basic cross-sectional image", by receiving a correcting operation or a confirming operation from the operator.

BRIEF DESCRIPTION OF THE DRAWINGS

FIG. 14 is a drawing for explaining a display example according to yet another embodiment.

DETAILED DESCRIPTION

An image processing apparatus according to an embodiment includes processing circuitry. The processing circuitry is configured to generate, from three-dimensional medical image data, a first cross-sectional image and a second cross-sectional image intersecting the first cross-sectional image and is configured to change display locations of the first cross-sectional image and the second cross-sectional image on a display, in conjunction with a change in an intersecting location of the first and the second cross-sectional images.

Exemplary embodiments of an image processing apparatus, a magnetic resonance imaging apparatus (hereinafter, "MRI apparatus", as necessary), and an image processing method will be explained below, with reference to the accompanying drawings. Possible embodiments are not limited to the exemplary embodiments described below. In principle, the description of each of the exemplary embodiments is similarly applicable to any other embodiment.

(First Embodiment)

Figure 1:
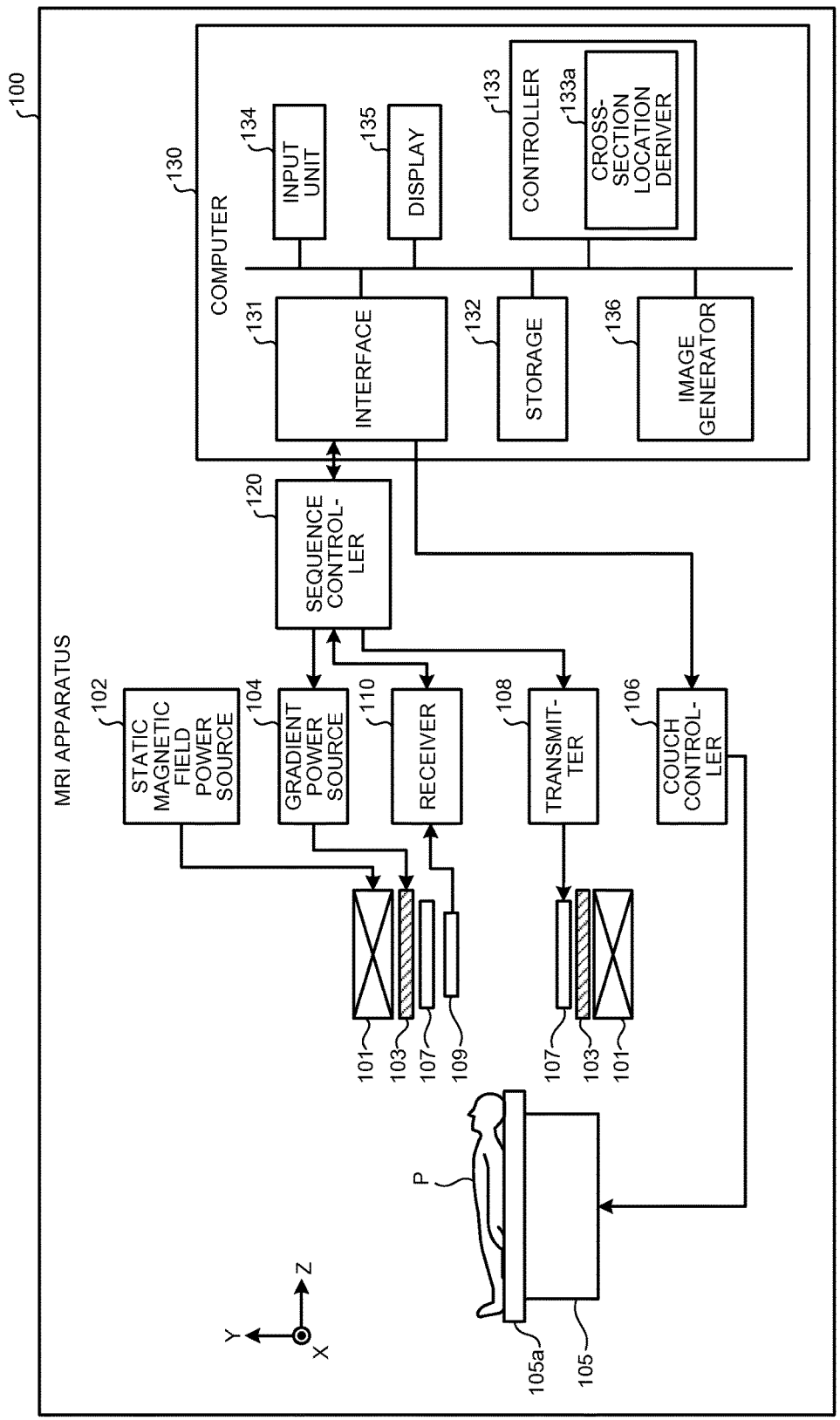
FIG. 1 is a block diagram of a Magnetic Resonance Imaging (MRI) apparatus according to a first embodiment.

FIG. 1 is a block diagram of an MRI apparatus 100 according to a first embodiment. As illustrated in FIG. 1, the MRI apparatus 100 includes a static magnetic field magnet 101, a static magnetic field power source 102, a gradient coil 103, a gradient magnetic field power source 104, a couch 105, a couch controller 106, a transmission coil 107, a transmitter 108, a reception coil 109, a receiver 110, a sequence controller 120, and a computer 130 (which may be called an "image processing apparatus"). The MRI apparatus 100 does not include an examined subject (such as a human body) P. The configuration illustrated in FIG. 1 is merely an example. In another example, any of the unit included in the sequence controller 120 and the computer 130 may be integrated together or separated, as appropriate.

The static magnetic field magnet 101 is a magnet formed in the shape of a hollow circular cylinder and is configured to generate a static magnetic field in the space on the inside thereof. The static magnetic field magnet 101 may be configured by using, for example, a superconducting magnet and is magnetically excited by receiving a supply of electric current from the static magnetic field power source 102. The static magnetic field power source 102 is configured to supply the electric current to the static magnetic field magnet 101. Alternatively, the static magnetic field magnet 101 may be configured by using a permanent magnet. In that situation, the MRI apparatus 100 does not need to include the static magnetic field power source 102. Further, the static magnetic field power source 102 may be provided separately from the MRI apparatus 100.

The gradient coil 103 is a coil formed in the shape of a hollow circular cylinder and is disposed on the inside of the static magnetic field magnet 101. The gradient coil 103 is formed by combining three coils corresponding to X-, Y-, and Z-axes that are orthogonal to one another. These three coils individually receive a supply of electric current from the gradient power source 104 and generate gradient magnetic fields of which the magnetic field intensities change along the X-, Y-, and Z-axes. The gradient magnetic fields on the X-, Y-, and Z-axes that are generated by the gradient coil 103 correspond to, for example, a slicing-purpose gradient magnetic field Gs, a phase-encoding-purpose gradient magnetic field Ge, and a reading-purpose gradient magnetic field Gr, respectively. The gradient power source 104 is configured to supply the electric current to the gradient coil 103.

The couch 105 includes a couchtop 105a on which the subject P is placed. Under control of the couch controller 106, while the subject P is placed thereon, the couchtop 105a is inserted into the hollow (i.e., an image taking opening) of the gradient coil 103. Normally, the couch 105 is provided so that the longitudinal direction thereof extends parallel to the central axis of the static magnetic field magnet 101. Under control of the computer 130, the couch controller 106 is configured to drive the couch 105 so that the couchtop 105a moves in longitudinal directions and in up-and-down directions.

The transmission coil 107 is provided on the inside of the gradient coil 103 and is configured to generate a radio frequency magnetic field by receiving a supply of a radio frequency (RF) pulse from the transmitter 108. The transmitter 108 is configured to supply the RF pulse corresponding to a Larmor frequency determined by the type of targeted atoms and the magnetic field intensities, to the transmission coil 107.

The reception coil 109 is provided on the inside of the gradient coil 103 and is configured to receive magnetic resonance signals (hereinafter, "MR signals", as necessary) emitted from the subject P due to an influence of the radio frequency magnetic field. When having received the MR signals, the reception coil 109 outputs the received MR signals to the receiver 110.

The transmission coil 107 and the reception coil 109 described above are merely examples. The configuration thereof may be realized by selecting one of the following or combining together two or more of the following: a coil having only a transmitting function; a coil having only a receiving function; and a coil having transmitting and receiving functions.

The receiver 110 is configured to detect the MR signals output from the reception coil 109 and to generate MR data on the basis of the detected MR signals. More specifically, the receiver 110 generates the MR data by applying a digital conversion to the MR signals output from the reception coil 109. Further, the receiver 110 is configured to transmit the generated MR data to the sequence controller 120. The receiver 110 may be provided on the gantry device side where the static magnetic field magnet 101, the gradient coil 103, and the like are provided.

The sequence controller 120 is configured to perform an image taking process on the subject P, by driving the gradient power source 104, the transmitter 108, and the receiver 110, on the basis of sequence information transmitted from the computer 130. In this situation, the sequence information is information that defines a procedure for performing the image taking process. The sequence information defines: the intensity of the electric current to be supplied from the gradient power source 104 to the gradient coil 103 and the timing with which the electric current is to be supplied; the strength of the RF pulse to be supplied by the transmitter 108 to the transmission coil 107 and the timing with which the RF pulse is to be applied; the timing with which the MR signals are to be detected by the receiver 110, and the like. For example, the sequence controller 120 may be configured with an integrated circuit such as an Application Specific Integrated Circuit (ASIC) or a Field Programmable Gate Array (FPGA) or an electronic circuit such as a Central Processing Unit (CPU) or a Micro Processing Unit (MPU).

Further, when having received the MR data from the receiver 110 as a result of the image taking process performed on the subject P by driving the gradient power source 104, the transmitter 108, and the receiver 110, the sequence controller 120 transfers the received MR data to the computer 130.

The computer 130 is configured to exercise overall control of the MRI apparatus 100, to generate an image, and the like. The computer 130 includes an interface 131, storage 132, a controller 133, an input unit 134, a display 135, and an image generator 136. Further, the controller 133 includes a cross-section location deriver 133a.

The interface 131 is configured to transmit the sequence information to the sequence controller 120 and to receive the MR data from the sequence controller 120. Further, when having received the MR data, the interface 131 is configured to store the received MR data into the storage 132. The MR data stored in the storage 132 is arranged into a k-space by the controller 133. As a result, the storage 132 stores therein k-space data.

The storage 132 is configured to store therein the MR data received by the interface 131, the k-space data arranged in the k-space by the controller 133, image data generated by the image generator 136, and the like. For example, the storage 132 is configured by using a Random Access Memory (RAM), a semiconductor memory element such as a flash memory, a hard disk, an optical disk, or the like.

The input unit 134 is configured to receive various types of instructions and inputs of information from an operator. For example, the input unit 134 is a pointing device such as a mouse or a trackball, a selecting device such as a mode changing switch, or an input device such as a keyboard. Under the control of the controller 133, the display 135 is configured to display a Graphical User Interface (GUI) used for receiving an input of an image taking condition and an image generated by the image generator 136, and the like. For example, the display 135 is a display device such as a liquid crystal display device.

The controller 133 is configured to exercise overall control of the MRI apparatus 100 and to control image taking processes, image generating processes, image display processes, and the like. For example, the controller 133 receives an input of an image taking condition (e.g., an image taking parameter) via the GUI and generates the sequence information according to the received image taking condition. Further, the controller 133 transmits the generated sequence information to the sequence controller 120. For example, the controller 133 is configured by using an integrated circuit such as an ASIC or an FPGA, or an electronic circuit such as a CPU or an MPU. Details of a process performed by the cross-section location deriver 133*a* will be described later.

The image generator 136 is configured to read the k-space data from the storage 132 and to generate an image by performing a reconstructing process such as a Fourier transform on the read k-space data.

Figure 2:
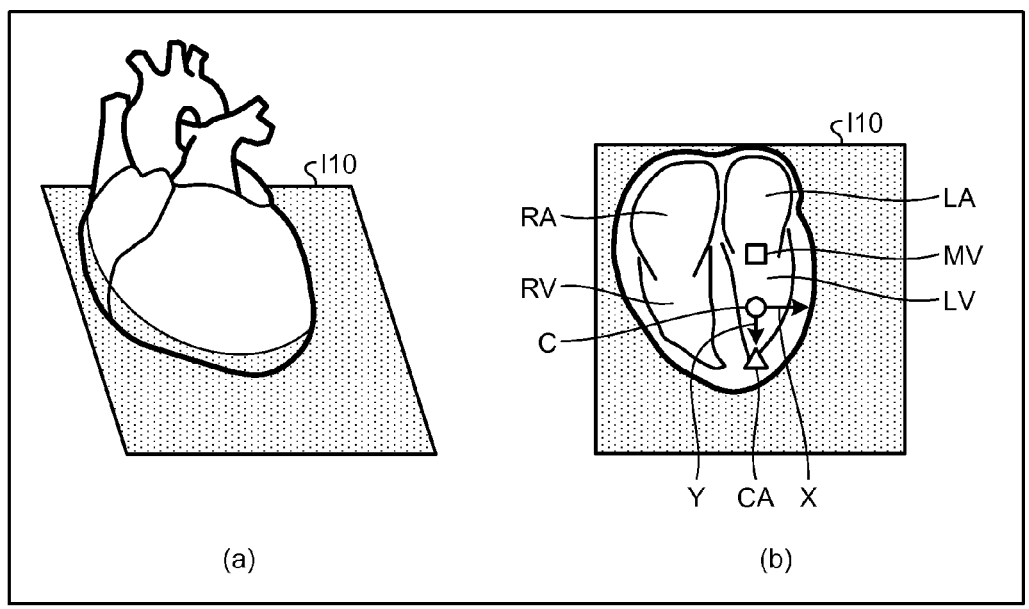
FIG. 2 is a drawing for explaining a basic cross-sectional image according to the first embodiment.
Figure 3:
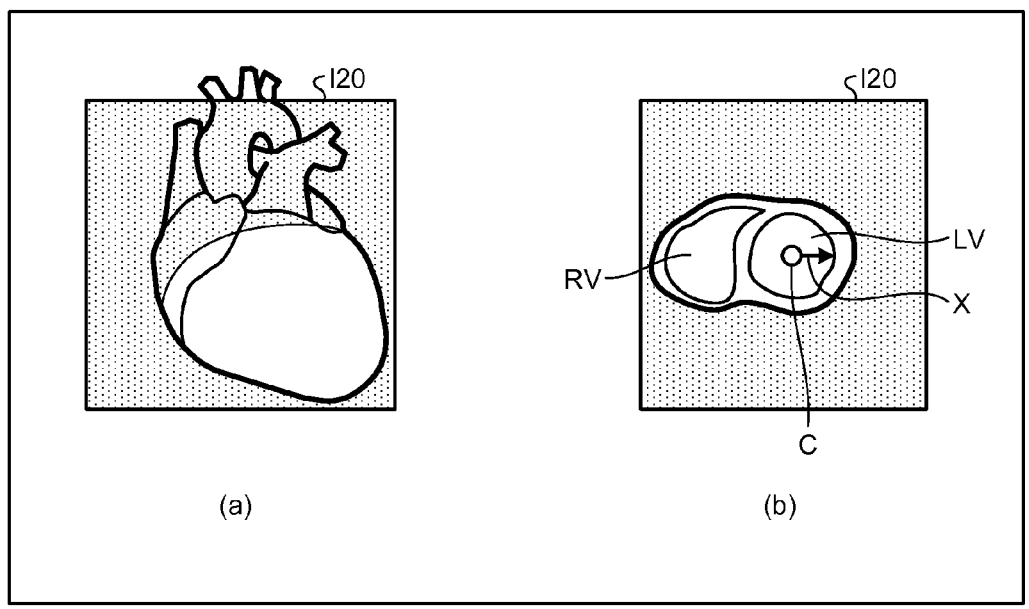
FIG. 3 is a drawing for explaining an auxiliary cross-sectional image according to the first embodiment.

FIG. 2 is a drawing for explaining a basic cross-sectional image according to the first embodiment. FIG. 3 is a drawing for explaining an auxiliary cross-sectional image according to the first embodiment. The first embodiment will be explained by using an example in which the "heart" is a target site, a "four-chamber cross-sectional image" is a basic cross-sectional image, and a "left ventricular short-axis image" is an auxiliary cross-sectional image. However, the basic cross-sectional image is not limited to a "four-chamber cross-sectional image" and may be any cross-sectional image that is set so as to include a desired site used in a diagnosis process. For example, the basic cross-sectional image may be a long-axis image such as a vertical long-axis image, a horizontal long-axis image, a two-chamber cross-sectional image, or a three-chamber cross-sectional image, or may be a left ventricular short-axis image. Similarly, the auxiliary cross-sectional image is not limited to a "left ventricular short-axis image" and may be any cross-sectional image that intersects the basic cross-sectional image.

FIG. 2(*a*) illustrates anatomical locating of a four-chamber cross-sectional image I10, whereas FIG. 2(*b*) illustrates an example of the four-chamber cross-sectional image I10. As illustrated in FIG. 2(*b*), the four-chamber cross-sectional image I10 is a cross-sectional image in which it is possible to view all the four chambers (i.e., the left ventricle (LV), the left atrium (LA), the right ventricle (RV), and the right atrium (RA)). Further, the four-chamber cross-sectional image I10 is a cross-sectional image that passes through the mitral valve (MV) and the cardiac apex (CA), which are characteristic sites of the heart. The part "C" in FIG. 2(*b*) denotes a site called "the center of the left ventricle" and is located at the middle point between the mitral valve (MV) and the cardiac apex (CA). A vector from the center of the left ventricle C to the cardiac apex CA will be referred to as a "long axis Y", whereas a vector that is orthogonal to the long axis Y on the four-chamber cross-sectional image I10 will be referred to as a "short axis X".

FIG. 3(*a*) illustrates anatomical locating of a left ventricular short-axis image I20, whereas FIG. 3(*b*) illustrates an example of the left ventricular short-axis image I20. As observed from FIGS. 2 and 3, the left ventricular short-axis image I20 is a cross-sectional image orthogonal to the long axis Y.

Figure 4:
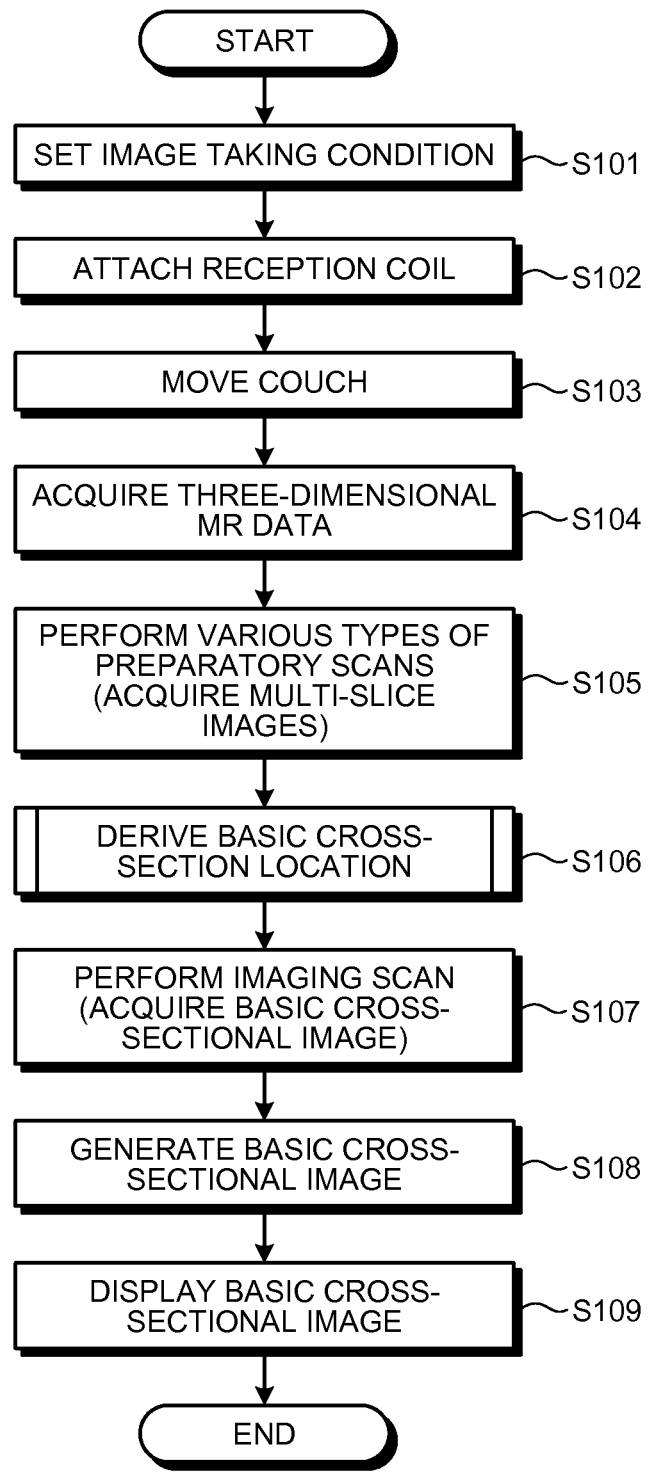
FIG. 4 is a flowchart of an overall processing procedure according to the first embodiment.

Next, FIG. 4 is a flowchart of an overall processing procedure according to the first embodiment.

First, the controller 133 receives an input of an image taking condition made by an operator, through a GUI via the input unit 134 and generates sequence information according to the received image taking condition (step S101). For example, as the GUI, the controller 133 displays a screen containing: an area to accept, on a model diagram of a human body, a selection for each image taking site; an area in which a generic name for a group of protocols (a pulse sequence) is displayed; and an area in which a list of protocols contained under each generic name is displayed. By using the GUI configured in this manner, the operator selects the "heart" from the model diagram of the human body according to a hierarchical structure of the areas, for example, and subsequently selects "Heart (four chambers)" as a generic term. After that, the operator selects protocols for various types of preparatory scans (e.g., a protocol for a preparatory scan performed to acquire image data for a location determining purpose) and an imaging scan protocol, from the list of protocols.

Next, the reception coil 109 is attached to the subject P, while the subject P is placed on the couchtop 105*a* of the couch 105, and the reception coil 109 is electrically connected to the MRI apparatus 100 (step S102). For example, the reception coil 109 is a body coil including a plurality of coil elements.

Subsequently, the couch controller 106 moves the couch 105 (step S103). More specifically, when the couch controller 106 has moved the couchtop 105*a* to a predetermined location, light from a projector (not illustrated) is radiated onto the subject P. At the time when the light from the projector is radiated onto the heart serving as an image taking site, the operator inputs a designation of the location of the image taking site via the input unit 134. Accordingly, the couch controller 106 moves the couchtop 105*a* in such a manner that the designated image taking site is located at the center of the magnetic field.

After that, the sequence controller 120 acquires three-dimensional MR data of a region including the heart, by controlling the execution of the pulse sequence on the basis of the sequence information (step S104). During the acquiring process, normally, MR data of the entire image taking region, which is relatively large, is acquired, while the subject P is holding his/her breath. For this reason, the sequence controller 120 acquires the three-dimensional MR data at a high speed in accordance with image taking parameters (a flip angle, a slice thickness, a phase encoding number, and the like) that realize the acquiring process at a high speed with a low resolution. For example, the sequence controller 120 acquires the MR data by using a Gradient Echo (GE) type pulse sequence. Because the GE-type pulse sequence uses a method by which an excitation pulse and a gradient pulse having a small flip angle are applied, the Repetition Time (TR) thereof is shorter than the TR of a Spin Echo (SE) type pulse sequence. For example, the sequence controller 120 acquires the MR data by using a 3D Fast Field Echo (FFE).

The pulse sequence used for acquiring the three-dimensional MR data, however, is not limited to the 3D FFE. To acquire the three-dimensional MR data, the sequence controller 120 may use, as the pulse sequence, a 3D Steady-State Free Precession (SSFP) or a 3D Fast Asymmetric Spin Echo (FASE), for example. Alternatively, for example, the sequence controller 120 may acquire the three-dimensional MR data by performing a multi-slice image taking process that uses a 2D FFE, a 2D SSFP, or a 2D FASE. Further, for example, the sequence controller 120 may add a pulse sequence that applies a T2 preparation pulse, prior to the execution of any of these pulse sequences. By applying the T2 preparation pulse, it is possible to enhance the contrast of the image.

Further, for example, the sequence controller 120 acquires the three-dimensional MR data from an image taking region that is centered on the center of the magnetic field and that has a length of 25 cm or longer in the head-to-feet direction, the left-and-right direction, and the back-to-front direction of the subject P. In the first embodiment, because the three-dimensional MR data is acquired prior to other scans, it is unknown in what location and in what size the heart of the subject P will be rendered within the three-dimensional MR data. It is therefore necessary to set the image taking region to a somewhat large region. In this regard, because the dimension of the heart is considered to be approximately 13 cm in the head-to-feet direction, the image taking region in the first embodiment is arranged to be 25 cm or longer, which is approximately double the dimension of the heart. If the subject P is an infant, because the dimension of the heart is also supposed to be smaller, the image taking region may be arranged to be 20 cm or longer, for example. The size of the image taking region may arbitrarily be changed. For example, the sequence controller 120 may acquire the three-dimensional MR data by using the largest Field Of View (FOV) that can be set for the MRI apparatus 100 (e.g., in such a range that is able to guarantee uniformity of the static magnetic field intensity).

The three-dimensional MR data acquired in this manner is, in the first embodiment, used for deriving an image taking region to be used in a preparatory scan that follows. More specifically, the three-dimensional MR data is used for deriving the image taking region to be used in the preparatory scan for acquiring multi-slice images. In the first embodiment, the multi-slice images are used as "location determining purpose data" for deriving an image taking location of the basic cross-sectional image (hereinafter, "basic cross-section location", as necessary) acquired in an imaging scan. Further, when the three-dimensional MR data acquired at step S104 is compared with multi-slice images acquired in the preparatory scan that follows, the multi-slice images are usually acquired with a higher spatial resolution than that of the abovementioned three-dimensional MR data.

After that, as illustrated in FIG. 4, the sequence controller 120 performs various types of preparatory scans (step S105). The preparatory scan for acquiring the multi-slice images will be explained. For example, the controller 133 at first detects an upper end location and a lower end location of the heart by applying, as necessary, an image processing technique for performing a template matching process or a pattern recognition process that employs a classifier, to the three-dimensional MR data acquired at step S104. Subsequently, the controller 133 derives a predetermined region including the upper end location and the lower end location of the heart, i.e., a location that is offset by a predetermined amount in the direction toward the head from the upper end location of the heart and a location that is offset by a predetermined amount in the direction toward the feet from the lower end location of the heart, as an image taking region in the slice direction. In this situation, the controller 133 uses predetermined fixed values for setting the image taking region in the left-and-right direction and in the back-to-front direction so that the image taking region includes at least the heart, for example. Further, the controller 133 may display a confirmation screen on the display 135 and determine an image taking region after receiving a confirmation or a correction from the operator. Further, the predetermined amounts for the offsets may arbitrarily be set by using a fixed value, a variable value, a value received from the operator, or the like.

After that, the sequence controller 120 acquires MR data of the multi-slice images, by performing a 2D FFE, a 2D SSFP, or a 2D FASE, for example, in accordance with the image taking region derived by the controller 133. During this acquiring process, the MR data is acquired with a high resolution so that it is possible to identify cross-sectional images of the heart. For this reason, the sequence controller 120 acquires the MR data of the multi-slice images according to image taking parameters (a flip angle, a slice thickness, a slice pitch, a phase encoding number, and the like) that are able to realize the acquiring process with a high resolution. After that, the image generator 136 generates volume data by reconstructing a plurality of axial cross-sectional images along the body axis direction of the subject P, from the acquired MR data. For example, the volume data is a group made up of twenty axial cross-sectional images reconstructed by the image generator 136. In this situation, the image generator 136 may apply an isotropization process (an interpolation process to arrange the spatial intervals in the x, y, and z directions to be at an equal distance) to the reconstructed volume data, before supplying the isotropized volume data to the subsequent processing stage, as volume data. Alternatively, the image generator 136 may supply the volume data to the subsequent processing stage without applying any isotropization process thereto.

Further, the sequence controller 120 performs other preparatory scans. For example, the sequence controller 120 performs a preparatory scan for acquiring profile data that indicates sensitivity levels in the direction in which the coil elements (or channels) are arranged, a preparatory scan for acquiring a sensitivity map that indicates a sensitivity distribution of the coil elements (or the channels), a preparatory scan for acquiring spectrum data for obtaining a center frequency of the RF pulse, a preparatory scan for obtaining a current value of an electric current to flow through a correction coil (not illustrated) for the purpose of adjusting the uniformity of the static magnetic field, and the like.

Subsequently, by using the volume data generated at step S105, the cross-section location deriver 133a performs a series of processes for deriving the image taking location of the basic cross-sectional image to be acquired in the imaging scan, i.e., the basic cross-section location (step S106). Details of the processes to derive the basic cross-section location will be explained later.

After that, the sequence controller 120 performs the imaging scan, by setting the basic cross-section location derived at step S106 (step S107). Subsequently, the image generator 136 generates a desired basic cross-sectional image from the MR data acquired by the sequence controller 120 (step S108), and the generated basic cross-sectional image is displayed on the display 135 (step S109).

The processing procedure described above is merely an example. For instance, the order in which the various types of preparatory scans are performed may arbitrarily be changed. For example, the sequence controller 120 may perform only the multi-slice image acquiring process for deriving the basic cross-section location at a stage prior to the basic cross-section location deriving process, and may perform other preparatory scans at a stage later than the basic cross-section location deriving process. Further, generally speaking, it is sufficient if the sensitivity map is acquired at any time prior to the image generating process. Thus, the sensitivity map does not necessarily have to be acquired prior to the imaging scan. Further, at least a part of the preparatory scans may be performed prior to the three-dimensional MR data acquiring process at step S104.

Further, in the first embodiment, the example is explained in which the image taking region for acquiring the multi-slice images is derived by using the three-dimensional MR data acquired at step S104; however possible embodiments are not limited to this example. For instance, it is acceptable to acquire and display axial images or coronal images on the display 135 and to receive an image taking region used for acquiring multi-slice images from the operator. Further, for example, the process of generating the basic cross-sectional image after performing the imaging scan and the process of displaying the generated basic cross-sectional image on the display 135 may be omitted as appropriate, depending on the mode of operation.

Further, in the first embodiment, the example is explained in which, to derive the image taking region of the multi-slice images, the scan for acquiring the three-dimensional MR data (step S104) and the scan for acquiring the multi-slice images (step S105) are both performed; however, possible embodiments are not limited to this example. Another mode is also acceptable in which only one of the scans is performed. In that situation, both the "image taking region of the multi-slice images" and the "basic cross-section location" are derived from the volume data acquired and generated from the one of the scans. Consequently, it is desirable to configure the sequence controller 120 to perform the one of the scans at a high speed and with a high resolution. Further, it is desirable to configure the sequence controller 120 to perform the one of the scans so as to realize a high contrast. In this situation, the "high contrast" refers to a state in which the difference in brightness distributions is large between the blood and the myocardia, for example. In the first embodiment, for example, when acquiring the three-dimensional MR data for the purpose of deriving the image taking region of the multi-slice images, the sequence controller 120 performs the image taking process according to a setting of a relatively smaller flip angle (e.g., approximately 15°), by prioritizing a high speed than the contrast. In contrast, in the first embodiment, when acquiring the multi-slice images, the sequence controller 120 performs the image taking process according to a setting of a relatively larger flip angle (e.g., approximately 60°), so as to realize a high contrast. As explained here, because it is possible to adjust the contrast according to the setting of the flip angle, which is one of the image taking parameters, the sequence controller 120 is able to perform the image taking process with the high contrast according to the flip angle that is set so as to realize the high contrast, even in the mode in which only one of the scans is performed.

Figure 5:
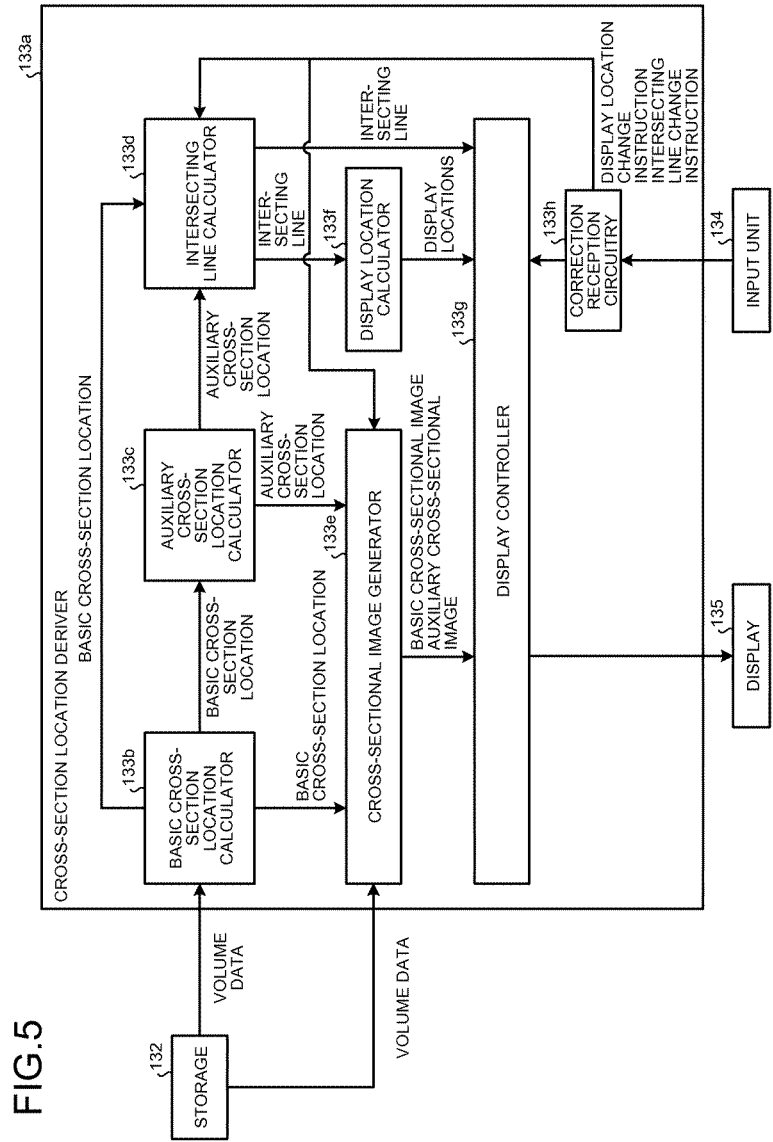
FIG. 5 is a block diagram of a cross-section location deriver according to the first embodiment.
Figure 6:
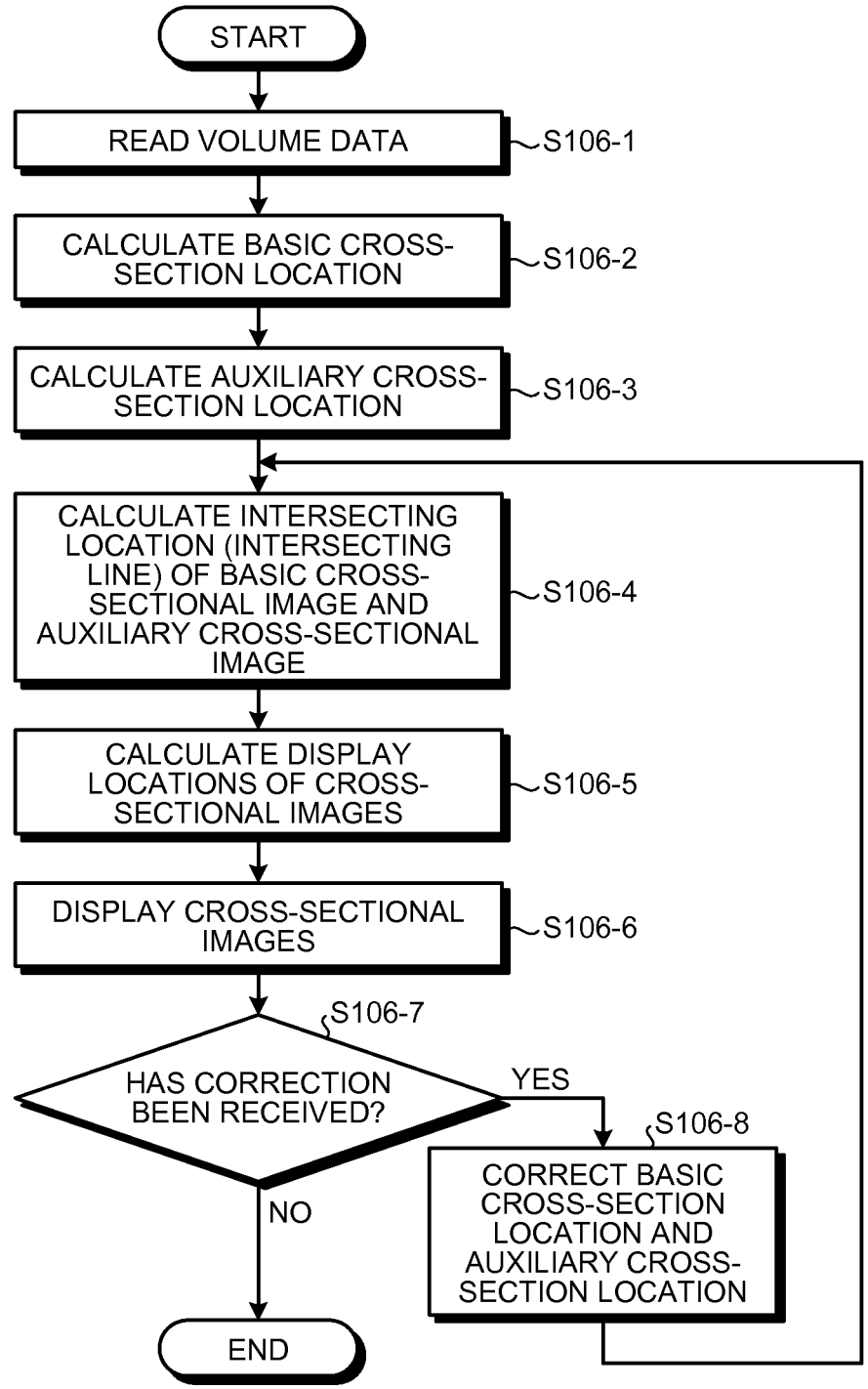
FIG. 6 is a flowchart of a processing procedure in a basic cross-section location deriving process according to the first embodiment.

Next, FIG. 5 is a block diagram of a cross-section location deriver 133a according to the first embodiment. FIG. 6 is a flowchart of a processing procedure in a basic cross-section location deriving process according to the first embodiment. The processing procedure illustrated in FIG. 6 corresponds to the process at step S106 in FIG. 4.

As illustrated in FIG. 5, the cross-section location deriver 133a according to the first embodiment includes a basic cross-section location calculator 133b, an auxiliary cross-section location calculator 133c, an intersecting line calculator 133d, a cross-sectional image generator 133e, a display location calculator 133f, a display controller 133g, and a correction reception circuitry 133h.

The basic cross-section location calculator 133b is configured to read the volume data from the storage 132 and to calculate a basic cross-section location indicating a spatial location of the basic cross-sectional image, by using the read volume data. Further, the basic cross-section location is an image taking location of the basic cross-sectional image acquired in the imaging scan. The basic cross-section location calculated by the basic cross-section location calculator 133b is used in processes performed by the auxiliary cross-section location calculator 133c, the intersecting line calculator 133d, and the cross-sectional image generator 133e.

The auxiliary cross-section location calculator 133c is configured, when having received the basic cross-section location from the basic cross-section location calculator 133b, to calculate an auxiliary cross-section location indicating a spatial location of an auxiliary cross-sectional image that intersects the basic cross-sectional image indicated by the basic cross-section location. The auxiliary cross-section location calculated by the auxiliary cross-section location calculator 133c is used in processes performed by the intersecting line calculator 133d and the cross-sectional image generator 133e.

The intersecting line calculator 133d is configured to calculate intersecting line information indicating an intersecting location of the basic and the auxiliary cross-sectional images, on the basis of the basic cross-section location received from the basic cross-section location calculator 133b and the auxiliary cross-section location received from the auxiliary cross-section location calculator 133c. The intersecting line information is information indicating the spatial location of the line on which the basic cross-sectional image and the auxiliary cross-sectional image intersect each other. Further, when having received an instruction to change the display location of the basic cross-sectional image or the auxiliary cross-sectional image or an instruction to change the intersecting line from the correction reception circuitry 133h, the intersecting line calculator 133d calculates intersecting line information corresponding to the details resulting from the change. The intersecting line information calculated by the intersecting line calculator 133d is used in processes performed by the display location calculator 133f and the display controller 133g.

The cross-sectional image generator 133e is configured to generate the basic cross-sectional image on the basis of the volume data read from the storage 132 and the basic cross-section location received from the basic cross-section location calculator 133b. Further, the cross-sectional image generator 133e is configured to generate the auxiliary cross-sectional image on the basis of the volume data read from the storage 132 and the auxiliary cross-section location received from the auxiliary cross-section location calculator 133c. Further, when having received an instruction to change the display location of the basic cross-sectional image or the auxiliary cross-sectional image or an instruction to change the intersecting line from the correction reception circuitry 133h, the cross-sectional image generator 133e calculates a basic cross-section location or an auxiliary cross-section location corresponding to the details resulting from the change. In other words, the cross-sectional image generator 133e calculates the basic cross-section location and the auxiliary cross-section location in accordance with a change in the relative locational relationship between the display locations in which the basic and the auxiliary cross-sectional images are displayed. Further, on the basis of the basic cross-section location or the auxiliary cross-section location calculated, the cross-sectional image generator 133e newly generates (re-generates) a basic cross-sectional image and/or an auxiliary cross-sectional image. The basic cross-sectional image and the auxiliary cross-sectional image generated by the cross-sectional image generator 133e are used in processes performed by the display controller 133g.

The display location calculator 133f is configured to receive the intersecting line information from the intersecting line calculator 133d and to calculate the display locations of the basic cross-sectional image and the auxiliary cross-sectional image in such a manner that the basic cross-sectional image is located in the extending direction of the intersecting line drawn in the auxiliary cross-sectional image. The display locations calculated by the display location calculator 133f are used in processes performed by the display controller 133g.

The display controller 133g is configured to display the basic cross-sectional image and the auxiliary cross-sectional image on the display 135, by arranging the two cross-sectional images to be located in the display locations of which the relative relationship is determined in accordance with the intersecting location of the two cross-sectional images. In other words, the display controller 133g changes display locations of the basic cross-sectional image and the auxiliary cross-sectional image, in conjunction with a change in the intersecting location of the two cross-sectional images. More specifically, the display controller 133g displays, on the display 135, the basic cross-sectional image and the auxiliary cross-sectional image received from the cross-sectional image generator 133e, according to the display locations received from the display location calculator 133f. Further, when displaying the basic cross-sectional image and the auxiliary cross-sectional image, the display controller 133g displays guide information indicating the extending direction of the intersecting line in a combined manner.

The correction reception circuitry 133h is configured to receive an instruction to change the display location of the basic cross-sectional image or the auxiliary cross-sectional image, or an instruction to change the intersecting line, from the operator via the input unit 134. The change instructions received by the correction reception circuitry 133h are used in processes performed by the intersecting line calculator 133d and the cross-sectional image generator 133e.

Details of the processes performed by the units described above will be explained according to the processing procedure illustrated in FIG. 6. First, the basic cross-section location calculator 133b reads the volume data from the storage 132 (step S106-1) and calculates the basic cross-section location (step S106-2). The basic cross-section location is the spatial location of the basic cross-sectional image in the three-dimensional image space and is expressed by parameters that are able to uniquely specify the basic cross-sectional image from the volume data.

For example, the parameters can be expressed by using the center point o (Expression (1)) of the basic cross-sectional image and two vectors u and v (Expression (2)) in the basic cross-sectional image. The two vectors u and v are able to uniquely specify the basic cross-section location unless the vectors u and v are parallel to each other.

$$o = (o_x, o_y, o_z) \tag{1}$$

$$\left.\begin{array}{l} u = (u_x, u_y, u_z) \\ v = (v_x, v_y, v_z) \end{array}\right\} \tag{2}$$

The basic cross-section location calculator 133b calculates the parameters o, u, and v, in such a manner that the desired site to be used in the diagnosis is included in the basic cross-sectional image. Further, in the first embodiment, the basic cross-section location calculator 133b calculates the center of the left ventricle C as the center point o of the basic cross-sectional image, calculates the short axis X as the vector u, and calculates the long axis Y as the vector v. The vectors u and v are two vectors that are orthogonal to each other. The vectors u and v, however, do not necessarily have to be two vectors orthogonal to each other.

In this situation, the basic cross-section location calculator 133b calculates the basic cross-section location by using a publicly-known technique. For example, the basic cross-section location calculator 133b specifies the center of the left ventricle C, the short axis X, and the long axis Y, by preparing a template image of the basic cross-sectional image in advance and performing a template matching process between the volume data and the template image. After that, the basic cross-section location calculator 133b calculates the parameters o, u, and v representing the center of the left ventricle C, the short axis X, and the long axis Y that were specified.

Further, for example, the basic cross-section location calculator 133b may specify the center of the left ventricle C, the short axis X, and the long axis Y, by preparing, in advance, a classifier that discriminates the basic cross-sectional image and applying the classifier to the volume data. In another example, the basic cross-section location calculator 133b may specify the center of the left ventricle C, the short axis X, and the long axis Y, by receiving designations of the center of the left ventricle C, the short axis X, and the long axis Y, from the operator.

The parameters do not necessarily have to be those corresponding to the center of the left ventricle C, the short axis X, and the long axis Y. The parameters may, for example, express locations of mutually-different three points in the basic cross-sectional image such as the mitral valve MV, the cardiac apex CA, and the short axis X. In yet another example, the parameters may express coordinate points of four vertices of a rectangle indicating a cross-sectional plane. In other words, it is acceptable to use any parameters as long as it is possible to uniquely specify the basic cross-sectional image out of the volume data.

Next, the auxiliary cross-section location calculator 133c calculates the auxiliary cross-section location by using the basic cross-section location calculated at step S106-2 (step S106-3). The auxiliary cross-sectional image is the cross-sectional image that intersects the basic cross-sectional image and that is auxiliarily used for aiding the process of setting the basic cross-sectional image (e.g., to make it easy for the operator to confirm the basic cross-section location). The auxiliary cross-section location is the spatial location of the auxiliary cross-sectional image in the three-dimensional image space and is expressed by parameters that are able to uniquely specify the auxiliary cross-sectional image from the volume data.

For example, the parameters are expressed by using the center point o' (Expression (3)) of the left ventricular short-axis image serving as the auxiliary cross-sectional image and two vectors u' and v' (Expression (4)) in the auxiliary cross-sectional image. The two vectors u' and v' are able to uniquely specify the auxiliary cross-section location unless the vectors u' and v' are parallel to each other. The variable "a" is an arbitrary constant, whereas "x" denotes the calculation of the vector product. As described in the first embodiment, by using the cross-sectional image orthogonal to the basic cross-sectional image as the auxiliary cross-sectional image, the operator is able to confirm the basic cross-section location more effectively.

$$o' = o + av \tag{3}$$

$$\left.\begin{array}{l} u' = u \\ v' = u \times v \end{array}\right\} \tag{4}$$

Subsequently, the intersecting line calculator 133d calculates the intersecting line information indicating the intersecting location of the two cross-sectional images, by using the basic cross-section location calculated at step S106-2 and the auxiliary cross-section location calculated at step S106-3 (step S106-4). For example, it is possible to calculate the intersecting line information in the auxiliary cross-sectional image, by projecting a vector of the intersecting line (hereinafter, "intersecting line vector") of the basic cross-sectional image and the auxiliary cross-sectional image onto the auxiliary cross-sectional image.

For example, by using Expression (5) the intersecting line calculator 133d calculates an intersecting line vector 1. The vector n is a normal vector of the basic cross-sectional image, whereas the vector n' is a normal vector of the auxiliary cross-sectional image. Further, the variable "b" is an arbitrary constant, whereas "p" denotes an arbitrary point on the interesting line of the basic cross-sectional image and the auxiliary cross-sectional image and can be calculated by solving equations of the planes of the basic cross-sectional image and the auxiliary cross-sectional image. Further, by projecting the intersecting line vector 1 calculated from Expression (5) onto the auxiliary cross-sectional image, the intersecting line calculator 133d is able to calculate the intersecting line information in the auxiliary cross-sectional image.

$$l=p+b(n\times n') \quad (5)$$

Subsequently, the display location calculator 133f calculates the display locations of the basic cross-sectional image and the auxiliary cross-sectional image in such a manner that the basic cross-sectional image is located in the extending direction of the intersecting line drawn in the auxiliary cross-sectional image (step S106-5).

Further, according to the display locations calculated at step S106-5, the display controller 133g displays the basic cross-sectional image and the auxiliary cross-sectional image on the display 135 (step S106-6). In addition, when displaying the basic cross-sectional image and the auxiliary cross-sectional image, the display controller 133g generates the guide information indicating the extending direction of the intersecting line and displays the generated guide information in a combined manner.

Prior to the display processing performed at step S106-6, the cross-sectional image generator 133e generates the basic cross-sectional image by using the volume data read from the storage 132 and the basic cross-section location calculated at step S106-2. Also, prior to the display processing performed at step S106-6, the cross-sectional image generator 133e generates the auxiliary cross-sectional image by using the volume data read from the storage 132 and the auxiliary cross-section location calculated at step S106-3. For example, the cross-sectional image generator 133e generates the basic cross-sectional image and the auxiliary cross-sectional image by applying Multi Planar Reconstruction (MPR) processing to the volume data, on the basis of the calculated basic and auxiliary cross-section locations.

Figure 7:
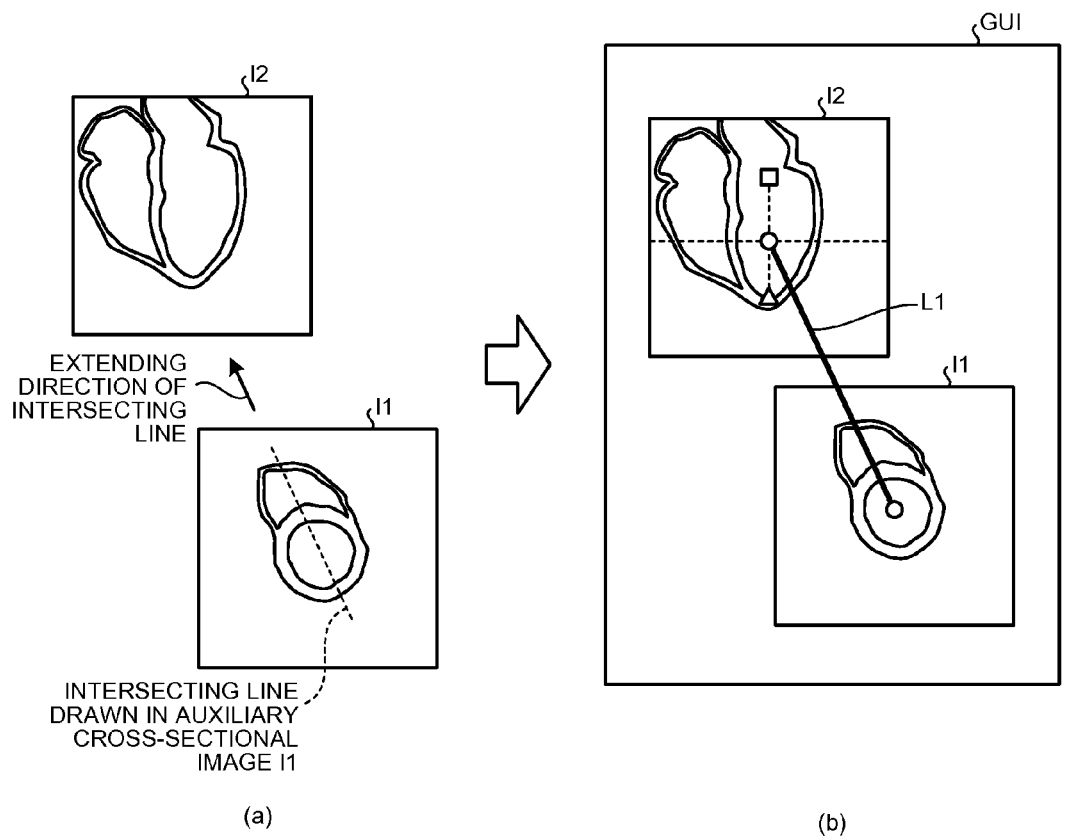
FIG. 7 is a drawing for explaining an example of displaying cross-sectional images according to the first embodiment.

FIG. 7 is a drawing for explaining an example of displaying the cross-sectional images according to the first embodiment. FIG. 7(a) is a drawing for explaining display locations of the cross-sectional images, whereas FIG. 7(b) is a drawing of a display example (a GUI). As illustrated in FIG. 7(a), the display controller 133g arranges an auxiliary cross-sectional image I1 and a basic cross-sectional image I2 in such a manner that the basic cross-sectional image I2 is to be located in an extending direction of an intersecting line drawn in the auxiliary cross-sectional image I1. In other words, in the first embodiment, the display controller 133g arranges the two cross-sectional images in such a manner that the basic cross-sectional image I2 is located in the direction of the short axis X in the auxiliary cross-sectional image I1. That is to say, in the first embodiment, the display controller 133g arranges the two cross-sectional images in such a manner that, on the straight line located at the angle at which the auxiliary cross-sectional image I1 is sliced, the basic cross-sectional image I2 corresponding to the slice is located.

FIG. 7(b) illustrates an example in which the display controller 133g causes the display 135 to display the single auxiliary cross-sectional image I1 and the single basic cross-sectional image I2. Further, in the first embodiment, as explained above, the center of the left ventricle C is used as the center point o of the basic cross-sectional image, whereas the center point o' of the auxiliary cross-sectional image is calculated by using Expression (3). As a result, as illustrated in FIG. 7(b), the auxiliary cross-sectional image I1 and the basic cross-sectional image I2 are both generated in such a manner that the center point thereof corresponds to the center of the left ventricle C. In the auxiliary cross-sectional image I1, the circle symbol corresponds to the center of the left ventricle C. In the basic cross-sectional image I2, the circle symbol corresponds to the center of the left ventricle C, while the square symbol corresponds to the mitral valve MV, and the triangle symbol corresponds to cardiac apex CA. Further, FIG. 7(b) illustrates the example in which the display controller 133g displays, in the basic cross-sectional image I2, a dotted line connecting together the square symbol, the circle symbol, and the triangle symbol, as well as another dotted line indicating an intersecting line with the auxiliary cross-sectional image I1 in the basic cross-sectional image I2.

Further, as illustrated in FIG. 7(b), the display controller 133g displays, in a combined manner, the guide information L1 indicating the extending direction of the intersecting line drawn in the auxiliary cross-sectional image I1. The guide information L1 indicates the extending direction of the intersecting line drawn in the auxiliary cross-sectional image I1, i.e., the direction of the short axis X in the auxiliary cross-sectional image I1 in the first embodiment. Further, in the first embodiment, the display controller 133g displays the guide information L1 as a line obtained by further extending the short axis X in the auxiliary cross-sectional image I1 to the outside of the auxiliary cross-sectional image I1, so as to connect the auxiliary cross-sectional image I1 and the basic cross-sectional image I2 together. For example, as illustrated in FIG. 7(b), the display controller 133g displays the guide information L1, so as to connect the center point of the auxiliary cross-sectional image I1 and the center point of the basic cross-sectional image I2 together.

Because the two cross-sectional images are displayed while being arranged in this manner, the operator who performs operations while viewing the two cross-sectional images is able to continuously correct and confirm the basic cross-section location, while his/her viewpoint moves little. Further, if the display controller 133g arranges the distance between the display locations of the two cross-sectional images to be as short as possible in such a range that the two cross-sectional images do not overlap each other (or in such a range that the sites of interest in the two cross-sectional images do not overlap each other), it is more effective because the viewpoint of the operator moves even less. Further, by viewing the display, the operator is able to intuitively understand in what spatial direction the short axis X in the basic cross-section location is set.

The display example illustrated in FIG. 7(b) is merely an example. For instance, the display controller 133g does not necessarily have to display the symbols indicating the center of the left ventricle C, the mitral valve MV, and the cardiac apex CA in the cross-sectional images. Further, for example, the display controller 133g does not necessarily have to display the two types of dotted lines drawn in the basic cross-sectional image I2. Further, for example, the display controller 133g may omit the guide line (guide information) L1. Further, although the guide line (guide information) L1 connects the center points of the two cross-sectional images together in the first embodiment, possible embodiments are not limited to this example. The guide line(guide information) L1 may connect together a center point and another point that is not a center point or may connect two points together neither of which is a center point. Further, for example, the display controller 133g may change the top-and-bottom relationship of the display locations between the auxiliary cross-sectional image I1 and the basic cross-sectional image I2. Further, for example, the display controller 133g may display the intersecting line itself in the auxiliary cross-sectional image I1, together with or in place of the guide information L1. In other words, it is acceptable for the display controller 133g to arbitrarily change the displayed state and the non-displayed state of any of the various types of information and the locational arrangements thereof.

Returning to the description of FIG. 6, after the basic cross-sectional image and the auxiliary cross-sectional image are displayed by the display controller 133g, the correction reception circuitry 133h judges whether a correction instruction has been received from the operator (step S106-7). If the correction reception circuitry 133h has received a correction instruction from the operator (step S106-7: Yes), a correction is subsequently made on the basic cross-section location and the auxiliary cross-section location on the basis of the correction instruction (step S106-8), and the processing returns to step S106-4. If the correction reception circuitry 133h has received no correction instruction from the operator (step S106-7: No), the processing performed by the cross-section location deriver 133a is ended, and the processing proceeds to step S107 illustrated in FIG. 4.

Figure 8:
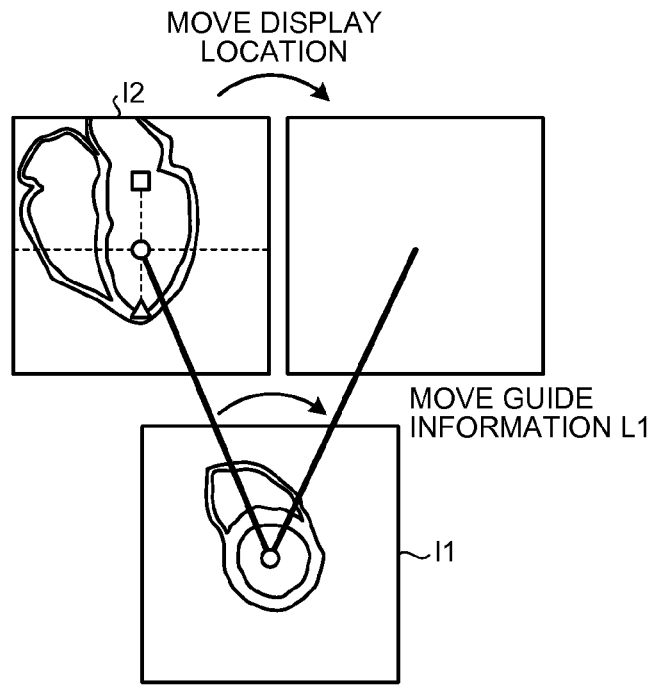
FIG. 8 is a drawing for explaining correcting a basic cross-section location and an auxiliary cross-section location according to the first embodiment.

FIG. 8 is a drawing for explaining correcting the basic cross-section location and the auxiliary cross-section location according to the first embodiment. There is a medical finding stating that, in a left ventricular short-axis image (which serves as the auxiliary cross-sectional image), the short axis X of a four-chamber cross-sectional image (which serves as the basic cross-sectional image) extends in such a direction that the short axis X goes through the corner of the right ventricle RV and the long axis Y. However, the shapes of the hearts vary among individuals. For this reason, the operator makes a minor correction of rotating the short axis X while using the long axis Y as the rotation axis, so that, in the left ventricular short-axis image, the short axis X of the four-chamber cross-sectional image goes through the corner of the right ventricle RV and the long axis Y.

For example, as illustrated in FIG. 8, the operator moves the display location of the basic cross-sectional image I2 displayed on the display 135, via the mouse included in the input unit 134. The correction reception circuitry 133h receives the moving operation as a display location change instruction and sends the received change instruction to the intersecting line calculator 133d and to the cross-sectional image generator 133e. The relationship between the intersecting line information and the display locations is known. Thus, on the basis of the post-move display locations (i.e., the relative relationship between the two cross-sectional images), the intersecting line calculator 133d re-calculates intersecting line information corresponding to the short axis X and sends the calculated intersecting line information to the display controller 133g. Further, the cross-sectional image generator 133e re-calculates the parameters of the basic cross-section location on the basis of the re-calculated intersecting line information and re-generates a basic cross-sectional image I2 from the volume data. Accordingly, the display controller 133g displays the re-generated basic cross-sectional image I2 in the post-move display location in the updated state, and displays guide information L1 so as to connect the center point of the auxiliary cross-sectional image I1 and the center point of the post-move basic cross-sectional image I2 together.

Further, for example, as illustrated in FIG. 8, the operator moves the guide information L1 displayed on the display 135 via the mouse included in the input unit 134. The correction reception circuitry 133h receives the moving operation as an intersecting line change instruction and sends the received change instruction to the intersecting line calculator 133d and to the cross-sectional image generator 133e. On the basis of the post-move guide information L1, the intersecting line calculator 133d re-calculates intersecting line information corresponding to the short axis X and sends the calculated intersecting line information to the display location calculator 133f and to the display controller 133g. The display location calculator 133f re-calculates a display location of the basic cross-sectional image in such a manner that the basic cross-sectional image is located in the extending direction of the re-calculated intersecting line. Further, the cross-sectional image generator 133e re-calculates the parameters of the basic cross-section location on the basis of the re-calculated intersecting line information and re-generates a basic cross-sectional image I2 from the volume data. Accordingly, the display controller 133g displays the re-generated basic cross-sectional image I2 in the post-move display location in the updated state, and displays guide information L1 so as to connect together the center point of the auxiliary cross-sectional image I1 and the center point of the post-move the basic cross-sectional image I2. If the intersecting line itself is displayed in the auxiliary cross-sectional image I1 together with or in place of the guide information L1, the correction reception circuitry 133h may receive a move of the intersecting line itself made by the operator as an intersecting line change instruction. In that situation, the display controller 133g displays a re-generated basic cross-sectional image I2 in the updated state in the display location calculated according to the intersecting line change instruction and displays a post-change intersecting line in the auxiliary cross-sectional image I1.

In the manner described above, the operator is able to appropriately set the basic cross-section location while making the minor correction of rotating the short axis X while using the long axis Y as the rotation axis. The corrections made on the basic cross-section location and the auxiliary cross-section location are not limited to the examples described in the embodiment above. For example, in the first embodiment, the method is explained by which the basic cross-sectional image I2 is moved, and the updating process is performed on the side of the basic cross-sectional image I2 that has been moved. However, possible embodiments are not limited to this example. For instance, another arrangement is acceptable in which a display location change instruction on the auxiliary cross-sectional image I1 side is received, so that an updating process is performed on the basic cross-sectional image I2 side. In another example, the display controller 133g may display basic cross-sectional images I2 in an accumulated manner (while the pre-move basic cross-sectional image I2 is continually displayed), according to an instruction from the operator, so that the plurality of basic cross-sectional images I2 are displayed next to one another. Further, for example, although the example in which the updating process is performed on the basic cross-sectional image side is explained in the first embodiment, possible embodiments are not limited to this example. It is acceptable to perform an updating process on the auxiliary cross-sectional image side or on both of the cross-sectional images, if necessary.

As explained above, according to the first embodiment, it is possible to easily perform the location determining process of the basic cross-sectional image. Because the basic cross-sectional image is located in the extending direction of the intersecting line drawn in the auxiliary cross-sectional image, the operator who performs operations while viewing the two cross-sectional images is able to continuously correct and confirm the basic cross-section location, while his/her viewpoint moves little. Further, according to the first embodiment, the guide line that connects the two cross-sectional images together is displayed in the combined manner. Because the guide line indicates the intersecting line in the auxiliary cross-sectional image, the operator is able to intuitively understand in what spatial direction the short axis X in the basic cross-section location is set. Further, because the guide line connects the two cross-sectional images together, the operator is able to move his/her viewpoint along the guide line.

Further, according to the first embodiment, the operator is able to confirm the new basic cross-sectional image resulting from the change in the basic cross-section location, only by performing the operation of moving the display location of the basic cross-sectional image or the guide line. Further, according to the first embodiment, because the updating process is performed only on the basic cross-sectional image side on which the move was made by the operator, it is possible to provide the GUI that is easy to understand for the operator.

(A First Alternative Display Example for the First Embodiment)

Figure 9:
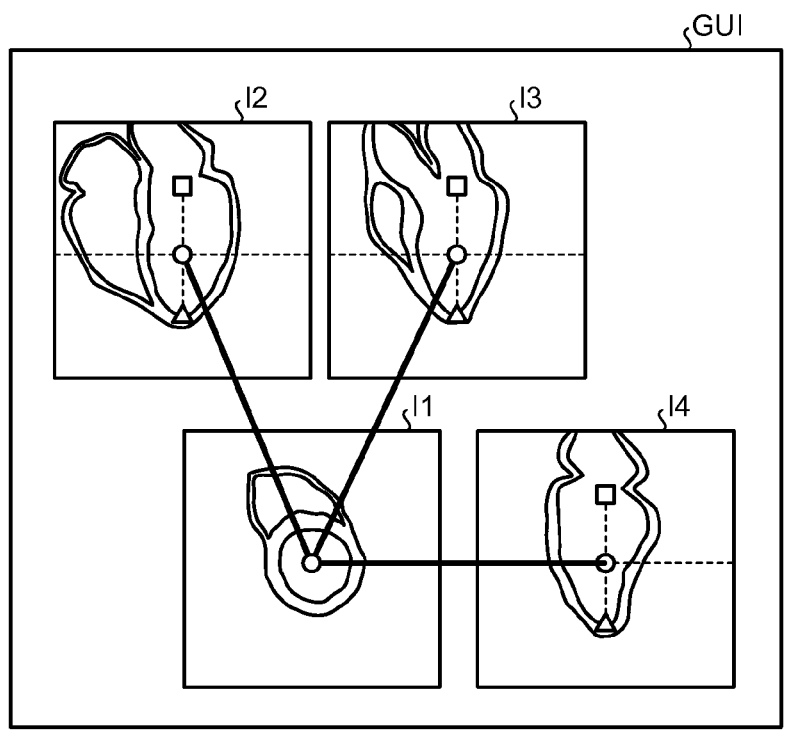
FIG. 9 is a drawing for explaining a first alternative display example for the first embodiment.

FIG. 9 is a drawing for explaining a first alternative display example for the first embodiment. In the first embodiment described above, the example is explained in which the display controller 133g displays the single auxiliary cross-sectional image I1 and the single basic cross-sectional image I2; however, possible embodiments are not limited to this example. For instance, with respect to the single auxiliary cross-sectional image I1, the display controller 133g may display a plurality of basic cross-sectional images I2 to I4 so as to be each located in the extending direction of the intersecting line thereof.

(A Second Alternative Display Example for the First Embodiment)

Figure 10:
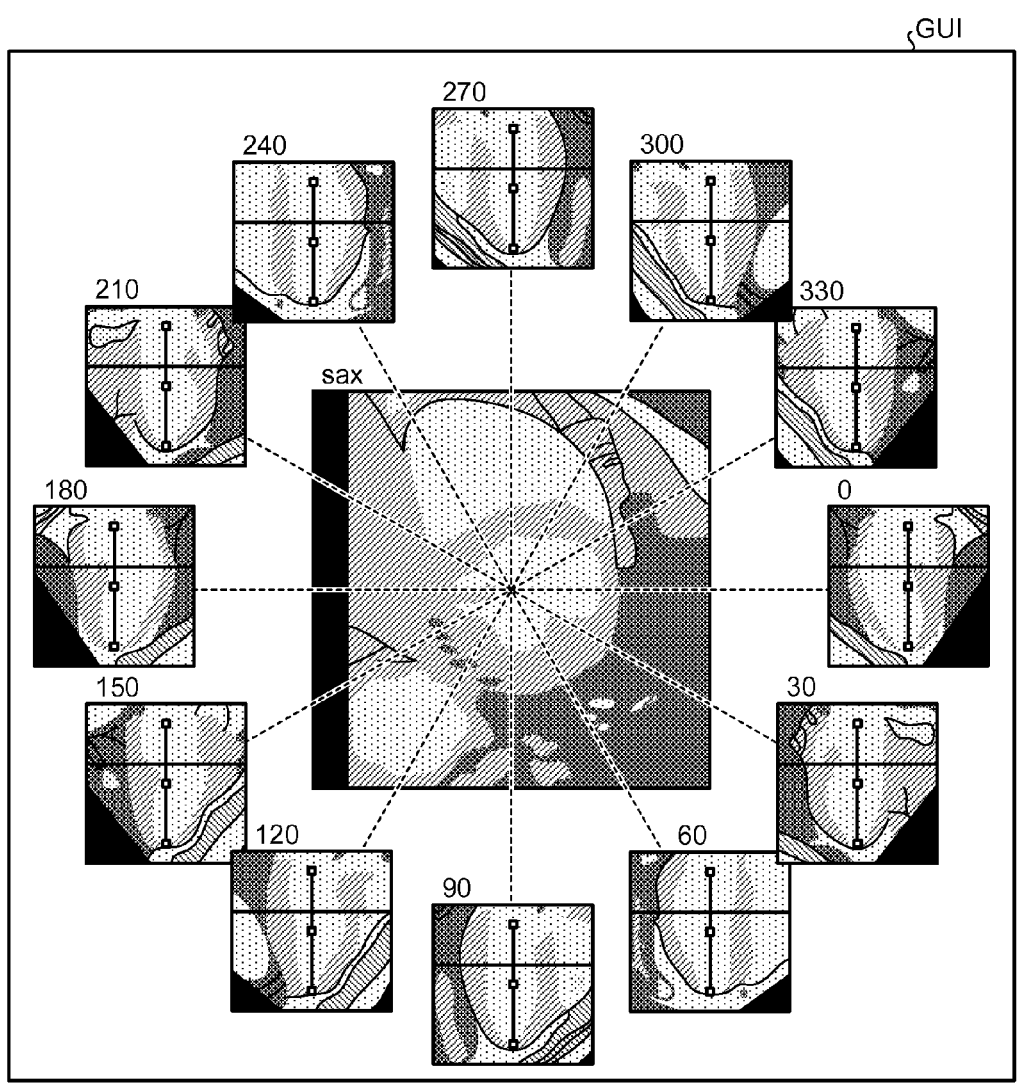
FIG. 10 is a drawing for explaining a second alternative display example for the first embodiment.

FIG. 10 is a drawing for explaining a second alternative display example for the first embodiment. For example, the display controller 133g may display a plurality of basic cross-sectional images obtained by rotating the short axis X by using the long axis Y as the rotation axis, so as to be located in the entire surrounding of a single auxiliary cross-sectional image. In FIG. 10, "sax" denotes a left ventricular short-axis image. Further, in FIG. 10, the numerals such as "270" denote the angles of the short axis X. Further, in FIG. 10, the dotted lines radially drawn from the center point of the auxiliary cross-sectional image to reach the basic cross-sectional images are guide lines. The transversal solid line drawn across each of the basic cross-sectional images is the intersecting line in the basic cross-sectional image. For example, from the operator, the display controller 133g receives an instruction indicating that basic cross-sectional images corresponding to an entire circumference be displayed at intervals of "30°" and realizes a display as illustrated in FIG. 10 according to the instruction. Alternatively, it is also acceptable to display a plurality of auxiliary cross-sectional images so as to be located in the entire surrounding of a single basic cross-sectional image.

(A Third Alternative Display Example for the First Embodiment)

Figure 11:
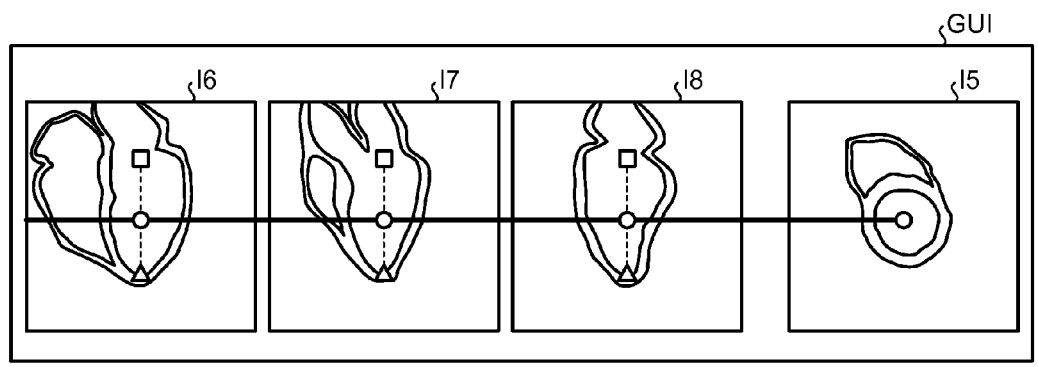
FIG. 11 is a drawing for explaining a third alternative display example for the first embodiment.

FIG. 11 is a drawing for explaining a third alternative display example for the first embodiment. For example, with respect to a single basic cross-sectional image I5, the display controller 133g may display a plurality of auxiliary cross-sectional images I6 to I8. In that situation, for example, as illustrated in FIG. 11, the display controller 133g displays, in a combined manner, a guide line which is a single straight line that connects together the center point of each of the auxiliary cross-sectional images I6 to I8 and the center point of the basic cross-sectional image I5.

(A Fourth Slternative Display Example for the First Embodiment)

Figure 12:
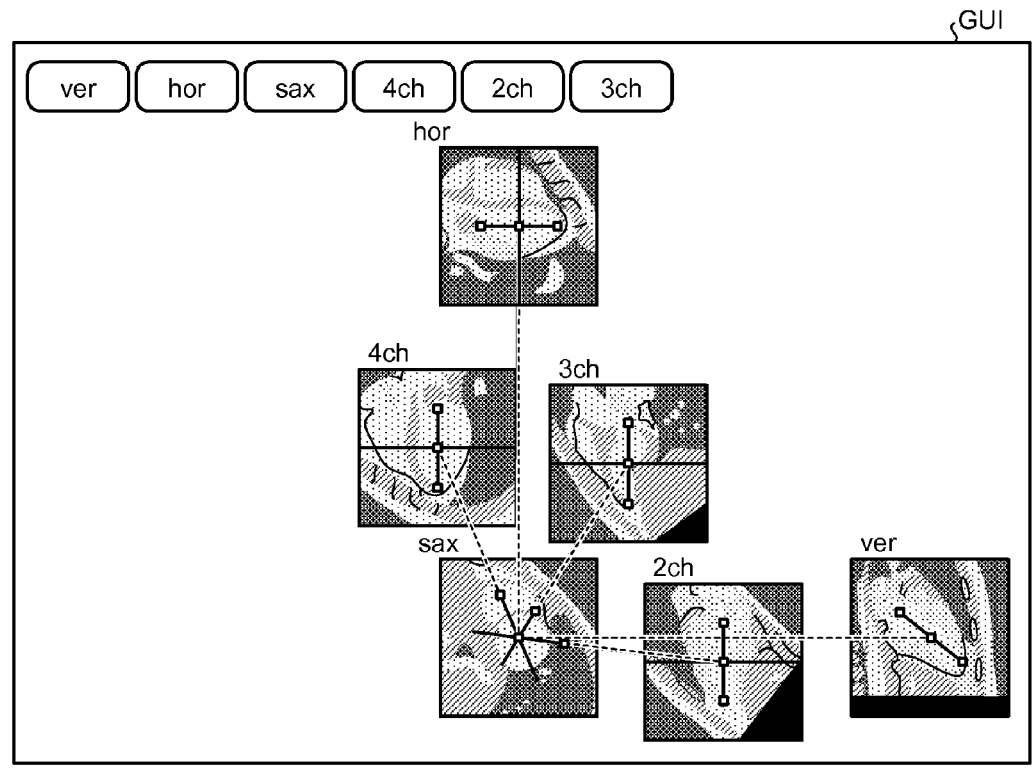
FIG. 12 is a drawing for explaining a fourth alternative display example for the first embodiment.

FIG. 12 is a drawing for explaining a fourth alternative display example for the first embodiment. For example, with respect to a single auxiliary cross-sectional image, the display controller 133g may display a plurality of types of basic cross-sectional images. In FIG. 12, "sax" denotes a left ventricular short-axis image, whereas "ver" denotes a vertical long-axis image, and "hor" denotes a horizontal long-axis image. Further, "4ch" denotes a four-chamber cross-sectional image, whereas "2ch" denotes a two-chamber cross-sectional image, and "3ch" denotes a three-chamber cross-sectional image. In FIG. 12, a plurality of types of basic cross-sectional images are displayed in the surrounding of the left ventricular short-axis image serving as an auxiliary cross-sectional image.

Further, as illustrated in FIG. 12, for example, the display controller 133g may display push buttons "ver", "hor", "sax", "4ch", "2ch", and "3ch" in a GUI. In accordance with whether any of the push buttons has been pressed by the operator or not, the display controller 133g is able to switch between a displayed state and a non-displayed state of the corresponding type of cross-sectional image. Because the display area of the GUI is limited, the operator is able to cause the cross-sectional images to be displayed by switching between the displayed state and the non-displayed state thereof, as appropriate. Alternatively, in accordance with whether any of the push buttons has been pressed by the operator or not, the display controller 133g may change the display order of the cross-sectional images. (For example, when two or more cross-sectional images overlap one another, the display order indicates which cross-sectional image should be displayed closest to the front or farthest in the back.)

(A Fifth Alternative Display Example for the First Embodiment)

By implementing the display in color, it is possible to arrange any of the various display examples described above to be visually recognized more easily. For example, in the second alternative display example illustrated in FIG. 10, by arranging the color of the frame of the auxiliary cross-sectional image "sax" to be the same (e.g., in light blue) as the color of the intersecting line in each of the basic cross-sectional images, the display controller 133g is able to help the operator to intuitively understand the relationship between the two. Further, for example, the display controller 133g may display the mitral valve MV (e.g., in red), the center of the left ventricle (e.g., in green), and the cardiac apex CA (e.g., in yellow) in distinguishable colors. The selection of the colors may arbitrarily be changed.

Further, in the fourth alternative display example illustrated in FIG. 12, the display controller 133g may arrange the color of each of the push buttons used for designating a type of cross-sectional image to be the same as the color of the frame of the corresponding cross-sectional image. For example, the display controller 133g may display the buttons "ver", "hor", "sax", "4ch", "2ch", and "3ch" in colors of "light yellow", "pink", "light blue", "red", "green", and "yellow", respectively, while displaying the frame of each corresponding cross-sectional image in the corresponding color. In that situation, the display controller 133g may also display the guide line connected to each of the cross-sectional images in the corresponding color. The selection of the colors may arbitrarily be changed.

(Other Embodiments)

Possible embodiments are not limited to the embodiments described above.

(Display Examples Using Three-Dimensionally Intersecting Images)

Figure 13A:
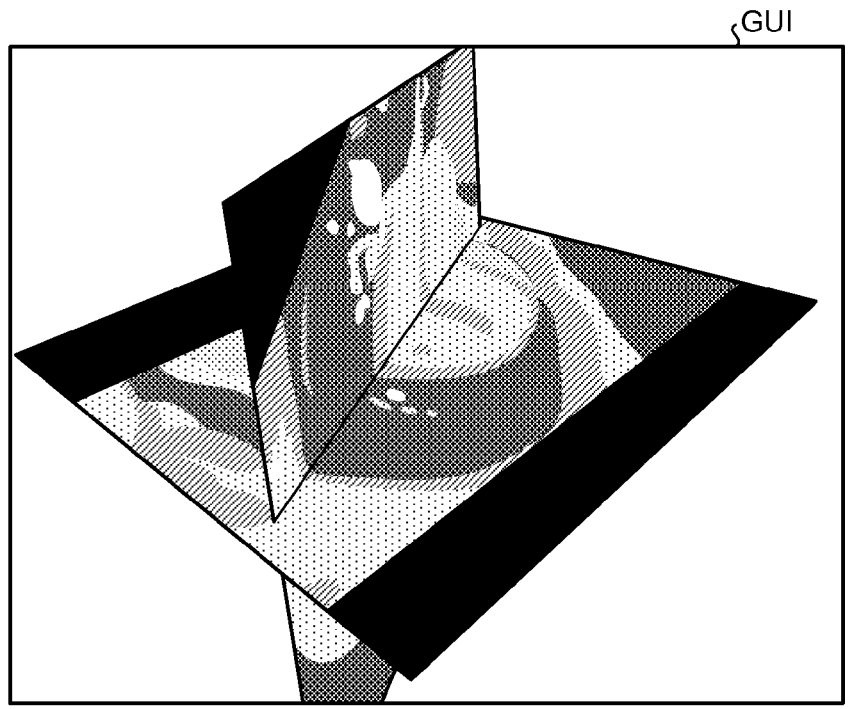
FIG. 13A is a drawing for explaining a display example according to another embodiment.
Figure 13B:
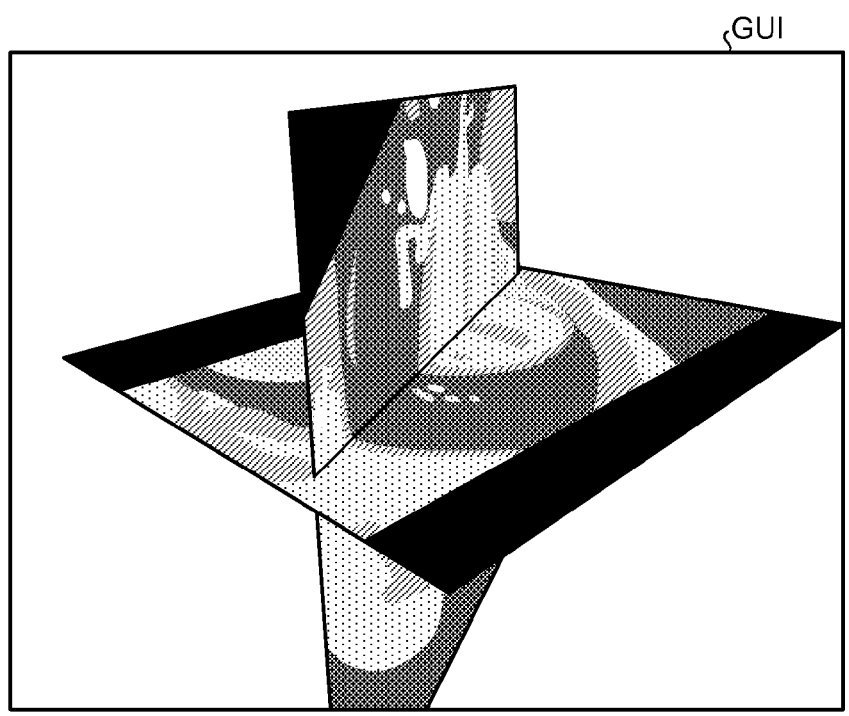
FIG. 13B is a drawing for explaining another display example according to said another embodiment.

FIGS. 13A and 13B are drawings for explaining display examples according to another embodiment. In the first embodiment, the example is explained in which, of the two cross-sectional images (i.e., the basic cross-sectional image and the auxiliary cross-sectional image), one of the cross-sectional images is located in the extending direction of the intersecting line drawn in the other cross-sectional image. However, possible embodiments are not limited to this example. As illustrated in FIGS. 13A and 13B, the display controller 133g may display a plurality of cross-sectional images in an arrangement where the plurality of cross-sectional images intersect each other three-dimensionally. In those situations also, the display controller 133g is configured to display the two cross-sectional images on the display 135, by arranging the cross-sectional images in the display locations of which the relative relationship is determined in accordance with the intersecting location of the two cross-sectional images.

The examples illustrated in FIGS. 13A and 13B are different from each other in terms of the intersecting location of the two cross-sectional images, i.e., the intersecting line information. Similarly to the first embodiment, the cross-sectional image generator 133e calculates the cross-section locations on the basis of the intersecting line information and generates the cross-sectional images from the volume data. The display controller 133g displays the corresponding cross-sectional images in accordance with the intersecting line information of the two cross-sectional images. Further, in accordance with a change in a relative relationship between display locations in which the two cross-sectional images are displayed (e.g., in accordance with a change from FIG. 13A to FIG. 13B), the cross-sectional image generator 133e re-generates at least one of the cross-sectional images from the volume data. After that, the display controller 133g replaces at least one selected from between the cross-sectional images with the re-generated cross-sectional image and displays the replaced re-generated cross-sectional image.

(Other Display Examples)

In the embodiments described above, the example is explained in which the basic cross-sectional image is located in the extending direction of the intersecting line drawn in the auxiliary cross-sectional image; however, possible embodiments are not limited to this example. For instance, the cross-sectional images may be displayed while being arranged next to one another in a transversal row. In that situation, for example, the display controller 133g displays, in a combined manner, guide lines each connecting a different one of a plurality of intersecting lines displayed in the auxiliary cross-sectional image to the one of the basic cross-sectional images corresponding to the intersecting line. By moving his/her viewpoint along the guide lines, the operator is able to find the basic cross-sectional image corresponding to any of the intersecting lines.

Further, FIG. 14 is a drawing for explaining a display example in yet another embodiment. In the display examples of the basic cross-sectional image and the auxiliary cross-sectional images described above, the method is explained by which the correction to be made on the basic cross-section location or the auxiliary cross-section location is received, while displaying the cross-sectional images at the time of the preparatory scan; however, possible embodiments are not limited to this example. Any of the display examples described above (e.g., FIGS. 7 to 13) is applicable as a display example that can be implemented after an imaging scan.

When displaying a basic cross-sectional image acquired in an imaging scan after the imaging scan, the display controller 133g changes the display locations of the basic cross-sectional image and an auxiliary cross-sectional image intersecting the basic cross-sectional image, in conjunction with a change in the intersecting location of the two cross-sectional images. For example, when the imaging scan has been performed and the basic cross-sectional image has been generated, the display controller 133g displays the basic cross-sectional image acquired in the imaging scan so as to be located in the extending direction of the intersecting line drawn in the auxiliary cross-sectional image acquired in a preparatory scan. For example, after the imaging scan has been performed, if an imaging scan is to be re-performed with a re-adjusted basic cross-section location so as to re-acquire a basic cross-sectional image, it is effective to implement the display in the manner described above after the imaging scan.

In the following sections, an example will be explained in which basic cross-sectional images have been taken in an imaging scan by performing a cine image taking process (successive image taking process in time series). For example, as illustrated in FIG. 14, with respect to an auxiliary cross-sectional image I11 calculated from volume data acquired in a preparatory scan, the display controller 133g displays each of a plurality of (or a plurality of types of) basic cross-sectional images I12 to I14 acquired in an imaging scan so as to be located in the extending direction of the intersecting line thereof. In that situation, the display controller 133g displays the auxiliary cross-sectional image I11 as a static picture and displays the basic cross-sectional images I12 to I14 in the manner of a cine display (displayed as a moving picture). In this situation, when displaying the basic cross-sectional images I12 to I14 in the manner of the cine display, the display controller 133g is also able to play back the basic cross-sectional images so that the cardiac phases thereof are synchronized with one another. If the basic cross-sectional images have a mutually equal number of phases (which corresponds to the number of cross-sectional images acquired in the cine image taking process), the display controller 133g is able to play back the basic cross-sectional images while the cardiac phases thereof are synchronized with one another by, for example, arranging the playback of all the basic cross-sectional images to start at the same time. Further, when the cross-sectional images are acquired by performing a cine image taking process while electrocardiogram is kept in synchronization therewith, because electrocardiogram (ECG) information is appended to the cross-sectional images, the display controller 133g is able to play back the basic cross-sectional images while the cardiac phases thereof are synchronized with one another by using, for example, the appended electrocardiogram information, even if the number of phases are different among the basic cross-sectional images.

For example, as illustrated in FIG. 14, while viewing the basic cross-sectional images I12 to I14 that have actually been acquired and are being displayed in the manner of the cine display, the operator moves the display location (or the guide information) of the basic cross-sectional image I13, via the mouse included in the input unit 134. Accordingly, the intersecting line calculator 133d re-calculates intersecting line information on the basis of the display location that is being moved (or that has been moved). Also, the cross-sectional image generator 133e re-calculates parameters of the basic cross-section location on the basis of the re-calculated intersecting line information and further generates the basic cross-sectional image I13 "from the volume data acquired in the preparatory scan". Because the basic cross-sectional image I13 is such a cross-sectional image that is generated from the volume data acquired in the preparatory scan, the basic cross-sectional image I13 is displayed as a static picture, and not in a cine display. For example, when the operator views the cine display of the basic cross-sectional image I13 and determines that it is a better idea to re-perform an image taking process by using a slightly-corrected basic cross-section location, it is effective to implement the method described above by which the basic cross-sectional image that was actually acquired and the basic cross-sectional image resulting from the correction of the basic cross-section location are displayed in the GUI. Further, by using mutually the same GUI for the preparatory scan and for the imaging scan, it is possible to improve the operability.

In addition, FIG. 14 also illustrates a method for changing the display size of the cross-sectional images, while the basic cross-sectional image I13 is being moved. Because the display area of the GUI is limited, the larger the number of cross-sectional images displayed in the GUI becomes, the smaller the display size of each cross-sectional image becomes. To cope with this situation, the display controller 133g adjusts display size of cross-sectional images, in such a manner that a display size of a cross-sectional image expected to be focused on by the operator from among the plurality of cross-sectional images being displayed is relatively larger than display sizes of the other cross-sectional images. For example, as illustrated in FIG. 14, the display controller 133g displays the basic cross-sectional image I13 in a larger display size (illustrated as a basic cross-sectional image I15 in FIG. 14) while the display location thereof is being moved by the operation of the operator. Further, the display controller 133g displays the other basic cross-sectional images I12 and I14 in reduced display sizes. Further, the display controller 133g does not change the display size of the auxiliary cross-sectional image I11. After that, when the moving of the basic cross-sectional image I13 has been completed, the display controller 133g displays the cross-sectional images by returning the display sizes thereof to the original display sizes.

The changing of the display sizes illustrated in FIG. 14 is merely an example. The display controller 133g may adjust display sizes of the cross-sectional images in such a manner that a display size of at least one selected from between a cross-sectional image being operated on and one or more cross-sectional images related to the cross-sectional image being operated on (e.g., a cross-sectional image that intersects the cross-sectional image being operated on) is relatively larger than display sizes of other cross-sectional images.

Further, in the display example described above, the example is explained in which the auxiliary cross-sectional image I11 is displayed as the static picture, whereas the basic cross-sectional images I12 to I14 are displayed in the manner of the cine display (displayed as the moving picture); however, possible embodiments are not limited to this example. For instance, if the auxiliary cross-sectional image I11 is also taken by performing a cine image taking process during an imaging scan, the display controller 133g is able to display the basic cross-sectional images I12 to I14 in the manner of a cine display, and also, to display the auxiliary cross-sectional image I11 in the manner of a cine display. Displaying both the auxiliary cross-sectional image and the basic cross-sectional images in the manner of the cine display is effective for re-adjusting the basic cross-section location. Further, similarly to the display example described above, when displaying the basic cross-sectional images I12 to I14 and the auxiliary cross-sectional image I11 in the manner of the cine display, the display controller 133g is also able to play back the cross-sectional images in such a manner that the cardiac phases thereof are in synchronization with one another.

Further, the changing of the display sizes described above is not limited to the display implemented after an imaging scan and is similarly applicable to other display examples described in the embodiments above (e.g., FIGS. 7 to 13). Further, applicable operations are not limited to the changing of the display sizes. The display controller 133g may exercise control so that at least one selected from between a cross-sectional image being operated on and one or more cross-sectional images related to the cross-sectional image being operated on is displayed, while other cross-sectional images are not displayed. In that situation, for example, when the operation is finished, the display controller 133g causes the other cross-sectional images that were controlled not to be displayed, to be displayed.

(A Method for Utilizing the Three-Dimensional MR Data (See Step S104 in FIG. 4))

In the first embodiment described above, the example is explained in which the image taking region used for acquiring the multi-slice images is derived by using the three-dimensional MR data acquired at step S104; however, possible embodiments are not limited to this example. The controller 133 may derive other image taking regions from the three-dimensional MR data acquired at step S104. For example, the controller 133 may detect a rectangular parallelepiped region that circumscribes the examined subject P from the three-dimensional MR data acquired at step S104, and may derive a region larger than the rectangular parallelepiped region as an image taking region used for taking a sensitivity map. In another example, the controller 133 may detect a rectangular parallelepiped region that circumscribes the heart from the three-dimensional MR data acquired at step S104 and may derive a predetermined region including the rectangular parallelepiped region as an image taking region used for a shimming image taking process.

(Other Sites)

In the first embodiment described above, the example is explained in which the "heart" is used as the target site; however, possible embodiments are not limited to this example. The present disclosure is similarly applicable to other situations where an image taking process is performed on other targets sites. For example, the present disclosure is similarly applicable to an image taking process performed on a joint such as a "shoulder" or a "knee". When an image taking process is performed on a shoulder joint, for example, a location determining process may be performed on a location-determining-purpose axial cross-sectional image so as to determine image taking locations of an oblique coronal cross-sectional image located parallel to the scapula and an oblique sagittal cross-sectional image orthogonal to the scapula. For example, from volume data acquired for the location determining purpose, the MRI apparatus 100 generates an axial cross-sectional image, as well as the oblique coronal cross-sectional image and the oblique sagittal cross-sectional image intersecting the axial cross-sectional image. Further, the MRI apparatus 100 displays the oblique coronal cross-sectional image so as to be located in the extending direction of an intersecting line with the oblique coronal cross-sectional image drawn in the axial cross-sectional image and displays the oblique sagittal cross-sectional image so as to be located in the extending direction of an intersecting line with the oblique sagittal cross-sectional image drawn in the axial cross-sectional image. After that, for example, in accordance with a change the relative relationship between the display locations of the two cross-sectional images (e.g., the axial cross-sectional image and the oblique coronal cross-sectional image), the MRI apparatus 100 updates at least one of the cross-sectional images (e.g., the oblique coronal cross-sectional image).

(Other Medical Image Diagnosis Apparatuses)

In the first embodiment described above, the example of the MRI apparatus 100 is explained; however, possible embodiments are not limited to this example. The processes described above are similarly applicable to other medical image diagnosis apparatuses such as X-ray CT apparatuses and ultrasound diagnosis apparatuses. For example, an X-ray CT apparatus may be configured to adopt the MPR processing as a post-processing process performed on acquired volume data and to generate and display desired cross-sectional images. In that situation, the X-ray CT apparatus is able to cause a display to display a plurality of cross-sectional images intersecting each other so as to be arranged in display locations of which the relative relationship is determined in accordance with the intersecting location of two cross-sectional images.

(Specific Numerical Values and the Order in Which Processes are Performed)

Essentially, the specific numerical values and the order in which the processes are performed presented in the above embodiments are merely examples. For instance, in the above embodiments, it is assumed that the heart is the target site of the diagnosis; however, possible embodiments are not limited to this example. Any site other than the heart may be used as the target site. Further, a plurality of sites may be used as target sites at the same time. Furthermore, the order in which the processes are performed and the specific pulse sequence may also arbitrarily be changed.

(An Image Processing System)

In the embodiments described above, the example is explained in which the medical image diagnosis apparatus performs the various types of processes; however, possible embodiments are not limited to this example. For instance, an image processing system that includes a medical image diagnosis apparatus and an image processing apparatus may perform the various types of processes described above. In this situation, the image processing apparatus may be, for example, a workstation, an image storing apparatus (an image server) or an image viewer used in a Picture Archiving and Communication System (PACS), any of various types of apparatuses used in an electronic medical record system, or the like. In that situation, for example, the medical image diagnosis apparatus acquires raw data such as MR data and projection data as well as volume data. Further, the image processing apparatus receives the raw data and the volume data acquired by the medical image diagnosis apparatus, from the medical image diagnosis apparatus, or from the image server via a network, or as an input from the operator via a recording medium, and stores the received data into a storage. After that, the image processing apparatus performs the various types of processes described above (e.g., the processes performed by the image generator 136 and the cross-section location deriver 133a) by using the raw data and the volume data stored in the storage as processing targets. The information about the cross-section locations and the like derived by the image processing apparatus is input back to the medical image diagnosis apparatus as necessary and will be used in a subsequent imaging scan or the like.

(Computer Programs)

Further, the instructions presented in the processing procedures described in the above embodiments may be executed according to a computer program (hereinafter, "program") realized with software. It is possible to achieve the same advantageous effects as those from the MRI apparatus 100 in the above embodiments, by causing a general-purpose computer to store the program therein in advance and to read the program. The instructions described in the above embodiments are recorded as a computer-executable program onto a magnetic disk (e.g., a flexible disk, a hard disk), an optical disk (e.g., a Compact Disk Read-Only Memory [CD-ROM], a Compact Disk Recordable [CD-R], a Compact Disk Rewritable [CD-RW], a Digital Versatile Disk Read-Only Memory [DVD-ROM], a Digital Versatile Disk Recordable [DVD±R], a Digital Versatile Disk Rewritable [DVD±RW]), a semiconductor memory, or the like. Any storage format can be used, as long as a computer or an incorporated system is able to read data from the storage medium. The computer is able to realize the same operations as those performed by the MRI apparatus 100 described in the above embodiments, by reading the program from the recording medium and having the CPU execute the instructions written in the program according to the read program. Further, when obtaining or reading the program, the computer may obtain or read the program via a network.

Further, according to the instructions in the program installed from the storage medium into the computer or the incorporated system, an Operating System (OS) working in the computer, middleware (MW) such as database management software or a network may execute a part of the processes performed for realizing the embodiments described above. Further, the storage medium does not necessarily have to a medium that is independent of the computer or the incorporated system. The storage medium may be such a storage medium that stores therein or temporarily stores therein the downloaded program transferred via a Local Area Network (LAN), the Internet, or the like. Further, the storage medium does not necessarily have to be one. Even the situation where the processes described in the above embodiments are executed from a plurality of media is included in possible modes of the storage medium implementing the embodiments. The medium/media may have any configuration.

Further, the computer or the incorporated system used in any of the embodiments is configured to execute the processes described in the above embodiments according to the program stored in the storage medium. The computer or the incorporated system may be configured by using a single apparatus such as a personal computer or a microcomputer or may be configured by using a system in which a plurality of apparatuses are connected together via a network. Furthermore, the computer used in any of the embodiments does not necessarily have to be a personal computer and may be an arithmetic processing apparatus, a microcomputer, or the like included in an information processing device. The term "computer" generally refers to any device or apparatus that is capable of realizing the functions described in the embodiments by using the program.

(A Hardware Configuration)

Figure 15:
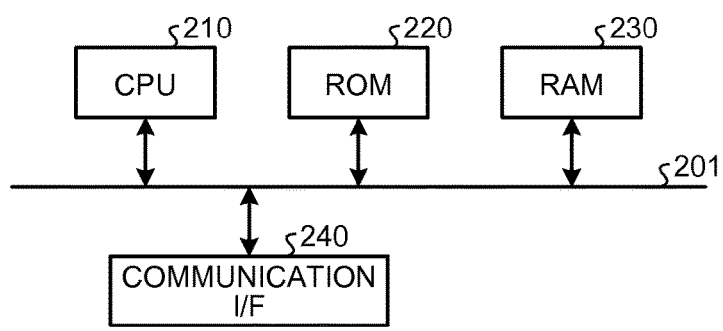
FIG. 15 is a diagram of a hardware configuration of an image processing apparatus according to an embodiment.

FIG. 15 is a diagram of a hardware configuration of an image processing apparatus according to an embodiment. The image processing apparatus according to the embodiments described above includes a controlling device such as a Central Processing Unit (CPU) 210, storage devices such as a Read-Only Memory (ROM) 220 and a Random Access Memory (RAM) 230, a communication interface (I/F) 240 that connects to a network and performs communication, and a bus 201 that connects the units together.

The program executed by the image processing apparatus according to the embodiments described above is provided as being incorporated, in advance, in the ROM 220 or the like. Further, the program executed by the image processing apparatus according to the embodiments described above is able to cause the computer to function as the units (e.g., the cross-section location deriver 133a) of the image processing apparatus described above. The computer is configured so that the CPU 210 is able to read the program from a computer-readable storage medium into a main storage device and to execute the read program.

According to at least one aspect of the image processing apparatus, the magnetic resonance imaging apparatus, and the image processing method described in the above embodiments, it is possible to appropriately set the cross-sectional images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising processing circuitry configured to:
   generate, from three-dimensional medical image data, a first cross-sectional image and a second cross-sectional image intersecting the first cross-sectional image;
   arrange, on a display, the first cross-sectional image to be located in an extending direction of an intersecting line with the first cross-sectional image drawn in the second cross-sectional image; and
   change display locations of the first cross-sectional image and the second cross-sectional image on the display, in conjunction with a change in an intersecting location of the first and the second cross-sectional images.

2. The image processing apparatus according to claim 1, wherein the processing circuitry is further configured to arrange the first cross-sectional image in a display location that does not cause the first cross-sectional image to overlap the second cross-sectional image.

3. The image processing apparatus according to claim 1, wherein the processing circuitry is further configured to display the first and the second cross-sectional images, and to display a guide line indicating the extending direction of the intersecting line.

4. The image processing apparatus according to claim 3, wherein the processing circuitry is further configured to display the guide line so as to connect the first and the second cross-sectional images together.

5. The image processing apparatus according to claim 1, wherein the processing circuitry is further configured to:
   generate, from the three-dimensional medical image data, the first cross-sectional image that is a basic cross-sectional image used for diagnosis of a heart and the second cross-sectional image that is an auxiliary cross-sectional image used when setting an image taking location of the basic cross-sectional image; and
   display the basic cross-sectional image so as to be located in an extending direction of an intersecting line with the basic cross-sectional image drawn in the auxiliary cross-sectional image; and
   display a guide line indicating the extending direction of the intersecting line so as to connect the basic and the auxiliary cross-sectional images together.

6. The image processing apparatus according to claim 1, wherein the processing circuitry is further configured to adjust display sizes of cross-sectional images in such a manner that a display size of at least one selected from between a cross-sectional image being operated on and one or more cross-sectional images related to the cross-sectional image being operated on is relatively larger than display sizes of other cross-sectional images.

7. The image processing apparatus according to claim 1, wherein the processing circuitry is further configured to exercise control so that at least one selected from between a cross-sectional image being operated on and one or more cross-sectional images related to the cross-sectional image being operated on is displayed, while other cross-sectional images are not displayed.

8. An image processing apparatus comprising processing circuitry configured to:
   generate, from three-dimensional medical image data, a first cross-sectional image and a second cross-sectional image intersecting the first cross-sectional image;
   change display locations of the first cross-sectional image and the second cross-sectional image on a display, in conjunction with a change in an intersecting location of the first and the second cross-sectional images;
   re-generate, from the medical image data, at least one selected from between the first and the second cross-sectional images, in accordance with a change in a relative relationship between display locations in which the first and the second cross-sectional images are displayed;
   replace at least one selected from between the first and the second cross-sectional images displayed on the display with the re-generated cross-sectional image; and
   display the replaced re-generated cross-sectional image.

9. An image processing apparatus comprising processing circuitry configured to:
   generate, from three-dimensional medical image data, a first cross-sectional image and a second cross-sectional image intersecting the trst cross-sectional image; and
   change dispay locations of the first cross-sectional image and the second cross-sectional image on a display, in conjunction with a change in an intersecting location of the first and the second cross-sectional images, wherein the processing circuitry is further configured to receive a change in a display location of at least one selected from between the first and the second cross-sectional images.

10. The image processing apparatus according to claim 9, wherein, from the medical image data, the processing circuitry is configured to re-generate said at least one of the cross-sectional images of which the change in the display location was received.

11. An image processing apparatus comprising processing circuitry configured to:
generate, from three-dimensional medical image data, a first cross-sectional image and a second cross-sectional image intersecting the first cross-sectional image; and
change display locations of the first cross-sectional image and the second cross-sectional image on a display, in conjunction with a change in an intersecting location of the first and the second cross-sectional images,
wherein the processing circuitry is further configured to receive a change in a guide line indicating an extending direction of an intersecting line with the first cross-sectional image drawn in the second cross-sectional image.

12. The magnetic resonance imaging apparatus comprising:
a sequence controller configured to acquire three-dimensional medical image data used when setting an image taking location of a cross-sectional image acquired by performing an imaging scan;
processing circuitry configured to:
generate a first cross-sectional image and a second cross-sectional image intersecting the first cross-sectional image, from the medical image data;
arrange, on a display, the first cross-sectional image to be located in an extending direction of an intersecting line with the first cross-sectional image drawn in the second cross-sectional image; and
change display locations of the first cross-sectional image and the second cross-sectional image on the display, in conjunction with a change in an intersecting location of the first and the second cross-sectional images.

13. The apparatus according to claim 12, wherein, when causing the display to display a third cross-sectional image acquired by performing the imaging scan after the imaging scan, the processing circuitry is further configured to change display locations of the third cross-sectional image and another cross-sectional image intersecting the third cross-sectional image, in conjunction with a change in an intersecting location of the third and the another cross-sectional images.

14. An image processing method implemented by an image processing apparatus, comprising:
generating, from three-dimensional medical image data, a first cross-sectional image and a second cross-sectional image intersecting the first cross-sectional image;
arranging, on a display, the first cross-sectional image to be located in an extending direction of an intersecting line with the first cross-sectional image drawn in the second cross-sectional image; and
changing display locations of the first cross-sectional image and the second cross-sectional image on the display, in conjunction with a change in an intersecting location of the first and the second cross-sectional images.

* * * * *